(12) United States Patent
Klieman et al.

(10) Patent No.: US 6,270,508 B1
(45) Date of Patent: Aug. 7, 2001

(54) END EFFECTOR AND INSTRUMENT FOR ENDOSCOPIC AND GENERAL SURGERY NEEDLE CONTROL

(76) Inventors: Charles H. Klieman, 21 Lochmoor La., Newport Beach, CA (US) 92660; David Needleman, 667 Sausalito Blvd., Sausalito, CA (US) 94965; John M. Stiggelbout, 89 Girard Ave., Sausalito, CA (US) 94965

( * ) Notice: Subject to any disclaimer, the term of this patent is extended or adjusted under 35 U.S.C. 154(b) by 0 days.

(21) Appl. No.: 09/426,207

(22) Filed: Oct. 25, 1999

Related U.S. Application Data
(60) Provisional application No. 60/105,594, filed on Oct. 26, 1998.

(51) Int. Cl.[7] .................................................. A61B 17/04
(52) U.S. Cl. .......................... 606/147; 606/207; 606/208
(58) Field of Search ..................... 606/205, 206, 606/207, 208, 147

(56) References Cited

U.S. PATENT DOCUMENTS

| | | | |
|---|---|---|---|
| 3,940,169 | * 2/1976 | Kock | 289/1.5 |
| 4,580,567 | * 4/1986 | Schweitzer et al. | 606/208 |
| 4,712,545 | 12/1987 | Honkanen . | |
| 5,174,300 | 12/1992 | Bales et al. . | |
| 5,209,747 | 5/1993 | Knoepfler . | |
| 5,275,615 | 1/1994 | Rose . | |
| 5,281,220 | 1/1994 | Blake, III . | |
| 5,282,807 | 2/1994 | Knoepfler . | |
| 5,282,826 | 2/1994 | Quadri . | |
| 5,308,358 | 5/1994 | Bond et al. . | |
| 5,318,589 | 6/1994 | Lichtman | 606/205 |
| 5,330,502 | 7/1994 | Hassler et al. | 606/205 |
| 5,350,391 | 9/1994 | Iacovelli | 606/170 |
| 5,374,277 | 12/1994 | Hassler | 606/207 |
| 5,383,888 | 1/1995 | Zvenyatsky et al. | 606/206 |
| 5,403,342 | 4/1995 | Tovey et al. | 606/205 |
| 5,409,498 | 4/1995 | Braddock et al. | 606/143 |

(List continued on next page.)

FOREIGN PATENT DOCUMENTS

| | | |
|---|---|---|
| 43 00 307 | 7/1994 | (DE) . |
| 43 07 539 | 9/1994 | (DE) . |
| WO 94/20034 | 9/1994 | (WO) . |
| WO 96/10957 | 4/1996 | (WO) . |

OTHER PUBLICATIONS

*Ethicon and You, The Ultimate Surgical Team*, Ethicon Endo–Surgery, Johnson & Johnson Co., pp. 3–74, Feb. 24, 1992.

*Primary Examiner*—Gary Jackson
(74) *Attorney, Agent, or Firm*—Fish & Richardson P.C., P.A.

(57) ABSTRACT

A surgical instrument for use in laparoscopy is provided, comprising a tubular member having a proximal end and a distal end, a first end effector piece pivotably mounted to the tubular member near the distal end of the tubular member, a second end effector piece disposed near the distal end of the tubular member and being slidable relative to the tubular member, wherein a surgical item, such as a suture needle, may be received between the first end effector piece and the second end effector piece and may be rolled substantially axially by axial translation of the second end effector piece with respect to the first end effector piece. In one embodiment, the end effector pieces may be provided with depressions in their face surfaces. In another embodiment, the surgical instrument may also include a handle assembly having a control lever and a rotation actuator. The tubular member may also be rotatably mounted on the handle. In another embodiment, the handle assembly may comprise a number of servomotors for effecting motion in the tubular barrel and the end effector pieces.

53 Claims, 21 Drawing Sheets

U.S. PATENT DOCUMENTS

| | | | |
|---|---|---|---|
| 5,456,695 | 10/1995 | Herve Dallemagne | 606/207 |
| 5,474,571 | 12/1995 | Lang | 606/205 |
| 5,490,819 | 2/1996 | Nicholas et al. | 600/201 |
| 5,514,157 | 5/1996 | Nicholas et al. | 606/206 |
| 5,582,617 | 12/1996 | Klieman et al. | 606/170 |
| 5,626,609 * | 5/1997 | Zvenyatsky et al. | 606/208 |
| 5,630,832 * | 5/1997 | Giordano et al. | 606/208 |
| 5,792,165 | 8/1998 | Klieman et al. | 606/170 |
| 5,817,119 | 10/1998 | Klieman et al. | 606/174 |
| 5,827,323 | 10/1998 | Klieman et al. | 606/205 |

* cited by examiner

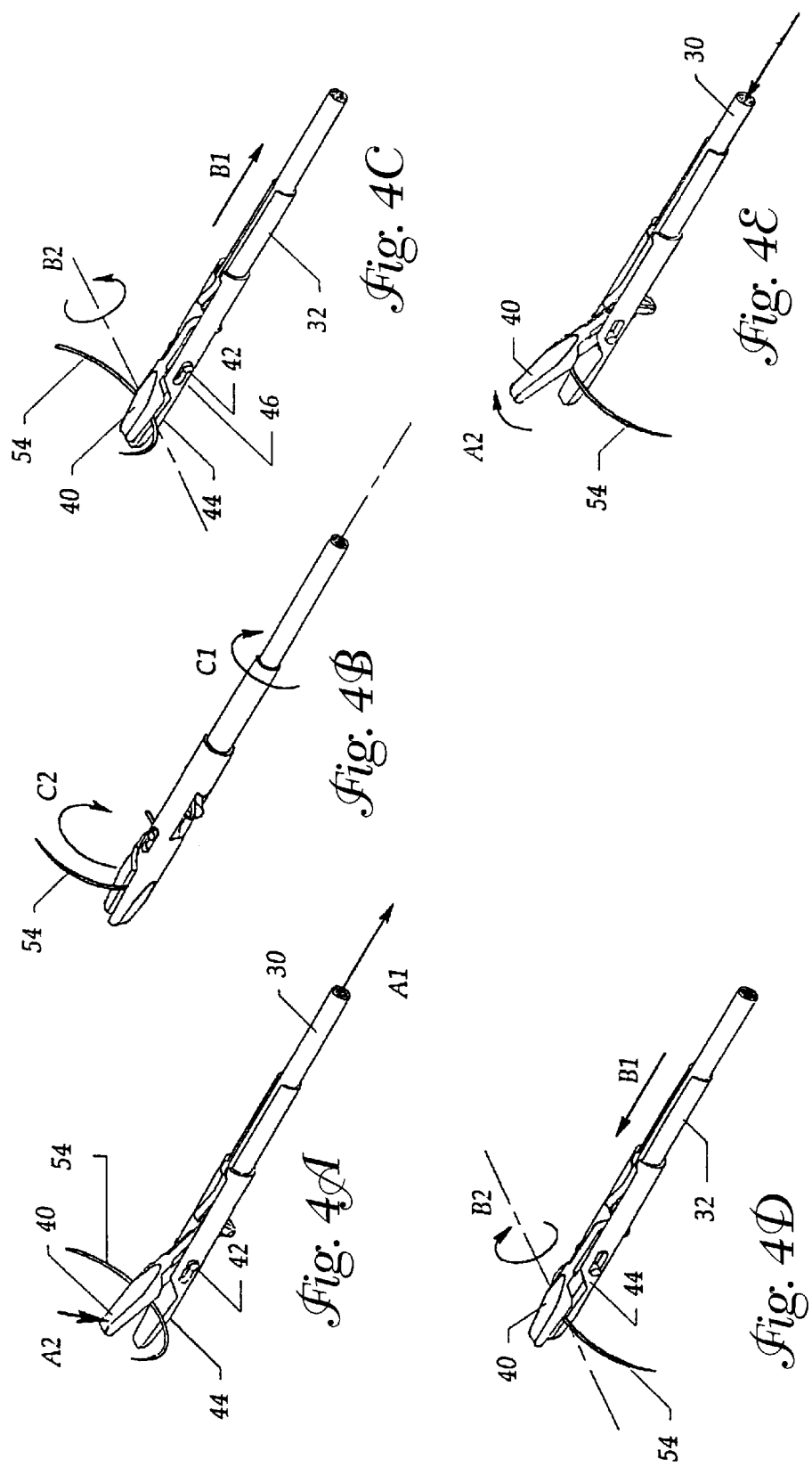

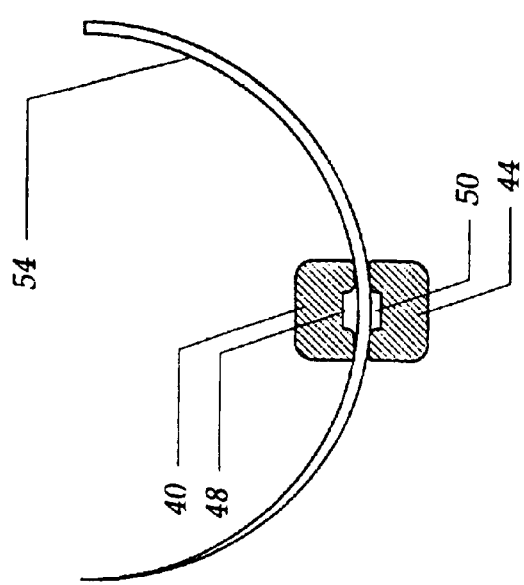
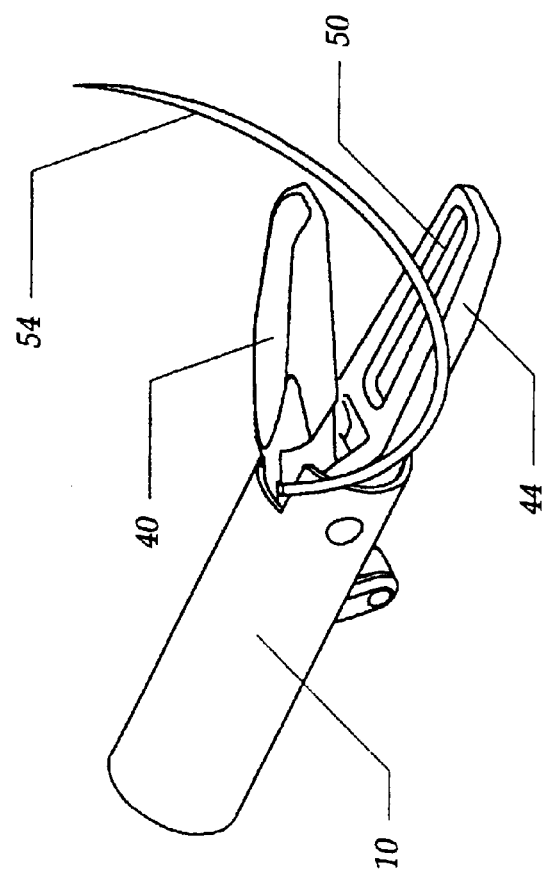

END EFFECTOR AND INSTRUMENT FOR ENDOSCOPIC AND GENERAL SURGERY NEEDLE CONTROL

RELATED APPLICATIONS

This application claims priority from U.S. Provisional Application Ser. No. 60/105,594, filed Oct. 26, 1998.

The present invention relates generally to the field of surgical instruments. In particular, it relates to an end effector of a surgical instrument for use in endoscopic surgical procedures.

BACKGROUND OF THE INVENTION

Endoscopy is a minimally invasive surgical procedure and includes, among other procedures, laparoscopy, thoracoscopy, and arthroscopy. Endoscopic procedures involve viewing the interior of the body using an illuminated optical instrument, referred to as an endoscope. The endoscope and other surgical instruments for operating on tissue inside the body enter the body through ports placed in small incisions in the skin.

Endoscopic procedures are typically conducted using specialized surgical instruments that have been adapted to perform general surgical procedures endoscopically. Endoscopic surgical instrument end effectors often take the form of a scissors, dissectors, or scissoring jaws, attached to the distal end of a rigid shaft. A handle attached to the proximal end of the shaft has a mechanism for operating the end effector. An operating linkage inside the shaft connects the handle to the end effector. The handle may also have a second mechanism for rotating the shaft and end effector.

Suturing is the preferred method of tissue approximation in endoscopic procedures. Suture needles are typically curvilinear in shape to facilitate stitching. One end of a suture needle is sharpened, and suture thread is attached to the other end of the needle. Because of restrictions on space and on instrument orientation, suture placement and tying of the suture thread involve difficult and awkward movements, making the process of suturing both lengthy and tedious. Surgical needle holders and needle drivers designed for endoscopic procedures generally have taken the form of an elongated tool designed to hold the suture needle rigidly and immovably in the surgical instrument. These holders and drivers enable the surgeon to hold and push the needle through tissue, but do not give the surgeon good needle mobility.

While the holders or drivers are typically comprised of a pair of jaws, they can take other forms, such as a gripper and anvil. A needle is typically grasped by the jaws midway between the tip of the needle and its tail. When a needle is first grasped in the jaws of a traditional needle holder, the needle may curve in any direction, whether upward, downward, distally, or proximally. In practice, the surgeon uses a second instrument, such as a forceps, a dissector, or another needle holder, to grasp and help orient the needle before suturing. This practice can be awkward and slow, and can also result in errors.

As surgeons become more proficient in conducting minimally invasive surgery, they are attempting to conduct more difficult and complex procedures laparoscopically. These newer procedures often require accurate suture placement. Present laparoscopic needle holders hold the needle firmly, but do not allow the operator to reorient the needle easily. In open surgery, where access is not restricted, this is not a problem. However, where access becomes restricted, such as in endoscopic procedures, needle re-orientation by the needle holder becomes more important.

SUMMARY OF THE INVENTION

In general, an end effector in accordance with the present invention includes a needle roller attached to a handle portion of a surgical instrument by an elongated tubular barrel. A handle on the handle portion may provide for holding the instrument and may also provide natural and precise control for grasping, rotating, and rolling a needle. The tubular barrel may be rotatably connected to the handle, and the needle roller may be disposed at the distal end of the tubular barrel. The handle may be configured to give full independence between the actions of rolling the needle, gripping the needle, and rotating the needle about the axis of the tubular barrel. Two linkage members may be disposed along the inner length of the tubular barrel and connect the end effector pieces with controls in the handle. In one embodiment, the end effector is plier-like and includes two jaws. The first jaw is pivotably attached to a pin affixed to the distal end of the tubular barrel. The first jaw is also coupled to the distal end of the first linkage member so that axial motion of the first linkage member causes the jaw to pivot open or closed.

In operation, the needle is grasped between the two jaws by pivoting the first jaw toward the second jaw. The first jaw is pivoted by pulling the first linkage member in a proximal direction. The first linkage member is coupled, at its proximal end, to a control actuator, in the form of a thumb trigger lever, mounted on the handle. When the thumb trigger lever is squeezed toward the handle, the first linkage member slides proximally inside the tubular barrel and thereby closes the first jaw. A trigger lock may also be provided to lock the thumb trigger lever to the handle and thus allow the surgeon to grasp and lock the jaws onto a needle.

The second jaw is a sliding jaw and is attached to the distal end of the second linkage member. The second jaw slides axially along with the second linkage member. Such axial motion of the second jaw causes a needle held between the jaws to roll. The second linkage member may be moved by operating a fingerwheel, a fingerloop, or a fingertrigger, in the handle, to which the second linkage member may be operably connected. The fingerwheel, when rotated by the surgeon's index finger, or the fingerloop or fingertrigger, when pushed or pulled by the surgeon's index finger, thus translates the second jaw.

The handle assembly may also take the form of a servomotor-powered set of actuators. Servomotors may be coupled to the tubular barrel and to each of the linkage members. The servomotors may be mounted transversely to the longitudinal axis of the tubular barrel or may be mounted parallel to the rotational axis of the tubular barrel.

The jaw surfaces may be coated with a high friction or abrasive surface to better hold the needle. The coating serves both to permit the jaws to grip the outside of the needle to facilitate rolling of the needle, and also to hold the needle securely in place to permit the surgeon to push the needle without it sliding in the jaws.

Suturing may also be aided by axial rotation of both jaws, i.e., rotation about the longitudinal axis of the tubular barrel. The tubular barrel is rotatably attached to the handle but is restrained from moving axially. Rotation is accomplished by, for example, applying rotational force with the index finger to a rotation knob attached to the tubular barrel, or by operating a servomotor coupled to the tubular barrel. Because the first jaw pivots on a pin that is attached to the tubular barrel and the second jaw extends from the tubular barrel, both jaws rotate when the tubular barrel rotates.

The jaws may also be provided with opposing internal pockets on their faces. Flat jaws often cause excess stress on a curvilinear needle because they force the portion of the needle that is between the jaws to straighten. In a disclosed embodiment, small recesses, or pockets, are formed on the interior surfaces of the jaws. A needle is allowed to curve slightly into these pockets and therefore undergoes less overall stress than if there were no pockets.

A device in accordance with the present invention can be capable of positioning a needle within the limited space provided by an endoscopic procedure. The device may also provide a simple, robust mechanism for achieving the needle-rolling function. The device may be reusable utilizing standard sterilization means, such as steam, gas, or soaking. The device is simple, yet it may provide precise and intuitive one-handed controls for changing the direction of curve of a needle, for rotating the needle, and for rigidly grasping the needle.

In one embodiment, a surgical instrument used in laparoscopy is provided, comprising a tubular member having a proximal end and a distal end, a first end effector piece pivotably mounted to the tubular member near the distal end of the tubular member, and a second end effector piece disposed near the distal end of the tubular member and being slidable relative to the tubular member and the first end effector piece, wherein a surgical item may be received between the first end effector piece and the second end effector piece and may be rolled substantially axially by axial translation of the second end effector piece with respect to the first end effector piece.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 4A–4E are isometric views of the end effector mechanism showing the jaws grasping, rolling, rotating, and releasing a suture needle.

FIGS. 5A and 5B show a particular geometry of the end effector jaws.

DESCRIPTION OF THE PREFERRED EMBODIMENTS

Figure 1:
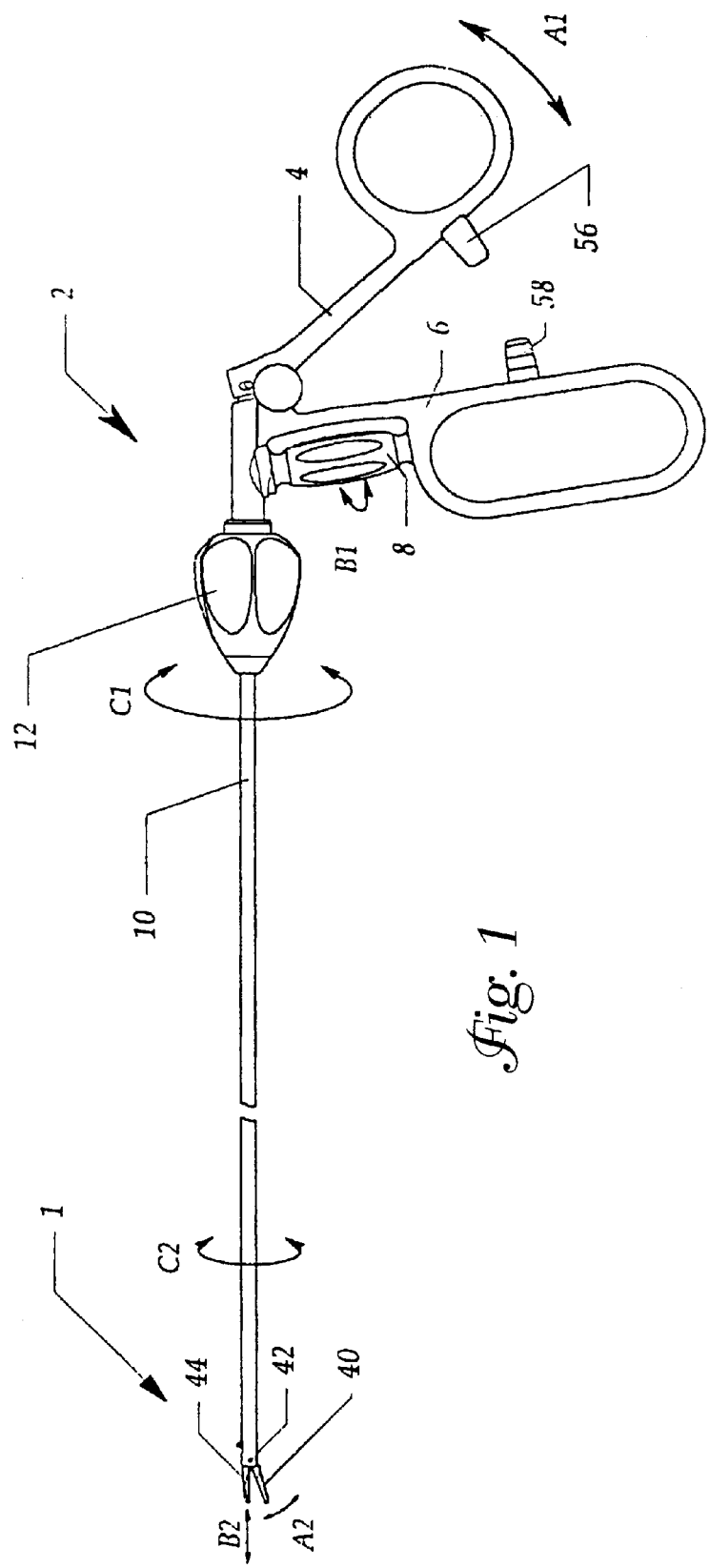
FIG. 1 is a left-side elevational view of the surgical instrument on which the needle roller end effector is mounted.

FIG. 1 is a left-side elevational view of a surgical instrument in accordance with the present invention. As shown in FIG. 1, the surgical instrument has a handle assembly 2 having a handle body 6 on which a trigger lever 4 is mounted. A rotation actuator, in the form of a rotation knob 12 and a rolling actuator, in the form of a pivoting fingerwheel 8, may also be provided on handle body 6. Generally, handle body 6 is held by a surgeon in either hand with a thumb through trigger lever 4, leaving the index finger to operate rotation knob 12 and fingerwheel 8. A tubular barrel 10 extends forward from handle assembly 2, with rotation knob 12 at its proximal end. The tubular barrel 10 also has disposed at its distal end an end effector 1 which consists of a pair of end effector pieces, shown in the figures as jaws 40, 44. A pin 42 pivotally attaches jaw 40 to the distal end of tubular barrel 10.

Handle assembly 2 may be configured to produce three separate motions in the end effector. First, rotation knob 12 may be turned to rotate tubular barrel 10 and thereby rotate end effector 1, as shown by rotation arcs C1 and C2. Second, trigger lever 4 may be squeezed toward handle assembly 2, as indicated by rotation arc A1, to cause jaw 40 to conduct a "grasping" motion relative to jaw 44, as indicated by rotation arc A2. Third, fingerwheel 8 may be rotated, as shown by rotation arc B1, to cause axial motion of jaw 44, as shown by arrow B2, so that a suture needle held laterally between jaw 40 and jaw 44 is caused to roll axially.

Figure 2:
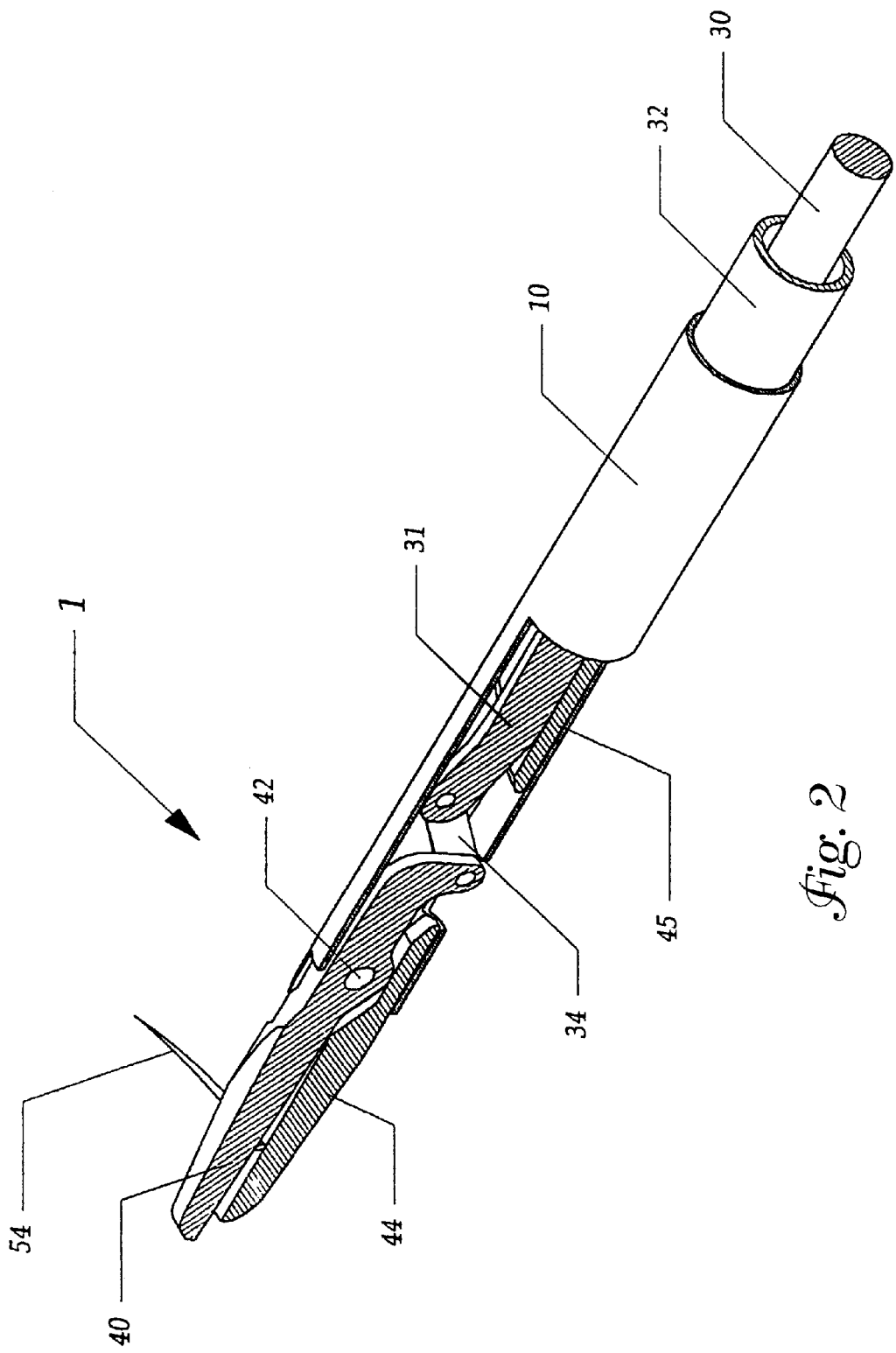
FIG. 2 is a sectioned isometric view of the end effector jaws.

FIG. 2 is an oblique view showing jaws 40, 44 holding a needle 54. Tubular barrel 10 is generally immovable and functions as a base and housing for end effector 1. clamping of needle 54 is accomplished through pivoting of jaw 40. Jaw 40 is pivotably mounted in an opening at the distal end of tubular barrel 10 on pin 42, which is positioned transverse to the longitudinal axis of tubular barrel 10. Pin 42 is mounted at each end in the wall of tubular barrel 10. Jaw 40 is connected by way of link 34 and link 31 to a linkage member, in the form of control rod 30, which is located coaxially with, and inside of, tubular barrel 10. Axial motion of control rod in the proximal direction, i.e., toward the handle assembly, draws link 31 and link 34 in the proximal direction, causing jaw 40 to pivot toward jaw 44. Axial motion of control rod 30 in the distal direction pushes link 31 and link 34, causing jaw 40 to pivot away from jaw 44.

Rolling of needle 54 is accomplished through axial motion of jaw 44. Jaw 44 extends from the distal end of tubular barrel 10 and is attached at its proximal end 45 to control tube 32. In the pictured embodiment, control tube 32 is coaxial with, and external to, control rod 30. In addition, control tube 32 is coaxial with, and internal to, tubular barrel 10. Control tube 32 and control rod 30 could also be positioned side-by-side. Axial motion of control tube 32 in the proximal direction causes axial motion of jaw 44 in the proximal direction, and axial motion of control tube 32 in the distal direction causes axial motion of control tube 32 in the distal direction. The position of jaw 44 is independent of the degree of closure of jaw 40.

Figure 3A:
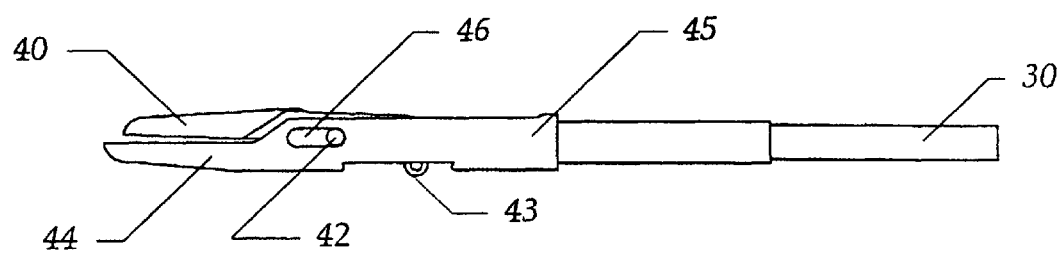
FIGS. 3A–3C are left-side elevation views of the end effector mechanism showing the grasping and rolling of a needle.

In FIG. 3A, the end effector mechanism is shown with the tubular barrel removed. A box-like cutout 43 is shown in the bottom of jaw 44 and a slot 46 is shown in the sides of jaw 44. Slot 46 allows free axial translation of jaw 44 relative to pivot pin 42. Pivot pin 42 is fixed to tubular barrel 10 and is pivotably connected to jaw 40.

Figure 3C:
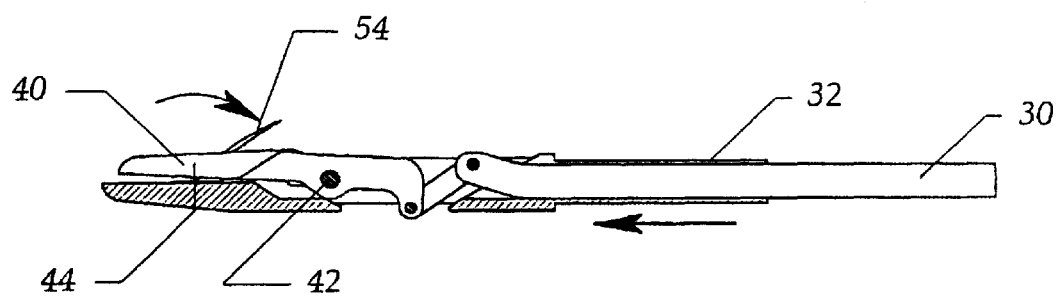
Figure 3B:
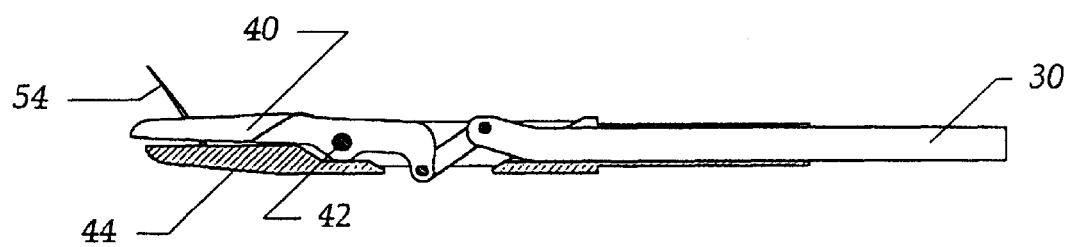

FIGS. 3B and 3C show the end effector assembly in operation in side cross-section. In FIG. 3B, needle 54 is shown firmly grasped in jaws 40, 44 and pinched between jaw 40 and jaw 44. Control rod 30 is shown pulled in the proximal direction so that jaw 40 clamps tightly against jaw 44. In FIG. 3C, control tube 32 is shown sliding in the distal direction relative to control rod 30 and pin 42. As jaw 44 is forced in the distal direction by control tube 32, the relative "shearing" between the surface of jaw 40 and the surface of jaw 44 causes needle 54 to roll axially in the distal direction and also to rotate clockwise. During rolling, jaw 40 is held closed against jaw 44 by control rod 30 in order to maintain friction between the surfaces of jaws 40, 44 and the outside of needle 54.

FIGS. 4A–4E show the various ways in which the end effector assembly may manipulate a needle. Tubular barrel 10, which provides support for pin 42, has been removed to better illustrate the components of the mechanism. FIG. 4A shows grasping of needle 54. Control rod 30 is pulled in a proximal direction shown by arrow A1, and thereby causes jaw 40 to pivot toward jaw 44 about pin 42, as shown by arrow A2. As jaw 44 pivots downward, it clamps down on needle 54.

FIG. 4B shows rotation of needle 54 about the longitudinal axis of the tubular barrel (not shown). Rotation of tubular barrel 10 (not shown in FIG. 4B), as shown by rotation arc C1, causes rotation of all the components of the end effector 10 mechanism, as shown by rotation arc C2. Rotation of needle 54 during grasping helps to produce a suturing motion.

FIG. 4C shows rolling of needle 54 with its axis perpendicular to the longitudinal axis of the tubular barrel (not shown). Control tube 32 is moved axially in the proximal direction, as shown by arrow B1, and thereby causes jaw 44 to slide in the proximal direction. Sliding of jaw 44 relative to jaw 40 with needle 54 clamped tightly between the jaws, causes rolling of needle 54 in the counter-clockwise direction as shown by rotation arc B2 and causes needle 54 to roll along the surface of jaw 40 in the proximal direction. During sliding of jaw 44, pin 42 slides freely inside slot 46.

FIG. 4D shows rolling of needle 54 in a direction opposite of that shown in FIG. 4C. Axial translation of control tube 32 in the distal direction causes axial translation of jaw 44 in the distal direction. Translation of jaw 44 relative to jaw 40 with needle 54 clamped tightly between jaws 40, 44 causes rotation of needle 54 in the clockwise direction, as shown by rotation arc B2, and causes needle 54 to move axially in the distal direction.

FIG. 4E shows release of needle 54. Axial motion of control rod 30 in the distal direction, as shown by arrow A1, causes jaw 40 to pivot upward away from jaw 44, as shown by arc A2.

FIGS. 5A and 5B illustrate configurations in jaw geometry to facilitate rolling of a curved needle. FIG. 5A shows a pocket 50 formed in the face of jaw 44. A similar pocket 48 is formed in the surface of jaw 40, as shown in the end sectional view of FIG. 5B. Because only the edges of the jaw surfaces contact needle 54, the grasping surfaces of jaw 40 and jaw 44 are reduced to pairs of line contact, resulting in smoother and easier needle roll from 0 degrees through 180 degrees. As a result, needle 54 is forced to distort less, and jaws 40, 44 are required to open less to accommodate the curvature of needle 54 as it passes through an angle roughly normal to jaws 40, 44.

Smooth and consistent rolling of needle 54, which is normally of a circular cross section or other geometric form with rounded corners, is aided by good contact between the needle surface and jaws 40, 44. Higher friction results in more positive rolling action and a firmer grip for suturing. Several materials traditionally have been used to surface jaws 40, 44 to improve needle gripping. Tungsten-carbide pads with a fine diagonal hatch may be brazed to the jaws. Alternatively, the jaw surfaces can be plated with diamond grit to achieve similar performance. To function effectively, the jaws ordinarily should hold the needle immovably. For a tight hold, the jaws should have a hard surface coating, and also be made of a material which is tough, high-strength, and corrosion resistant. The sliding jaw 44, in particular, is exposed to extremely high bending stresses when it is slid in the extreme distal position and then closed fully on a large needle. One exemplary material having such characteristics is a precipitation hardenable stainless alloy such as 17-4 PH or one of the 400-series alloys.

In general, the materials from which the other metallic parts of the present invention are formed are selected from appropriate materials such as stainless steel, and other high strength metallic alloys. The tubular barrel may be fabricated of stainless steel and the handle may also be fabricated of stainless steel, or molded of high strength engineering plastics or the like. Components and materials for this instrument may be selected from commercially available items, which those skilled in the art will be able to recognize and select as equivalent.

Figure 6:
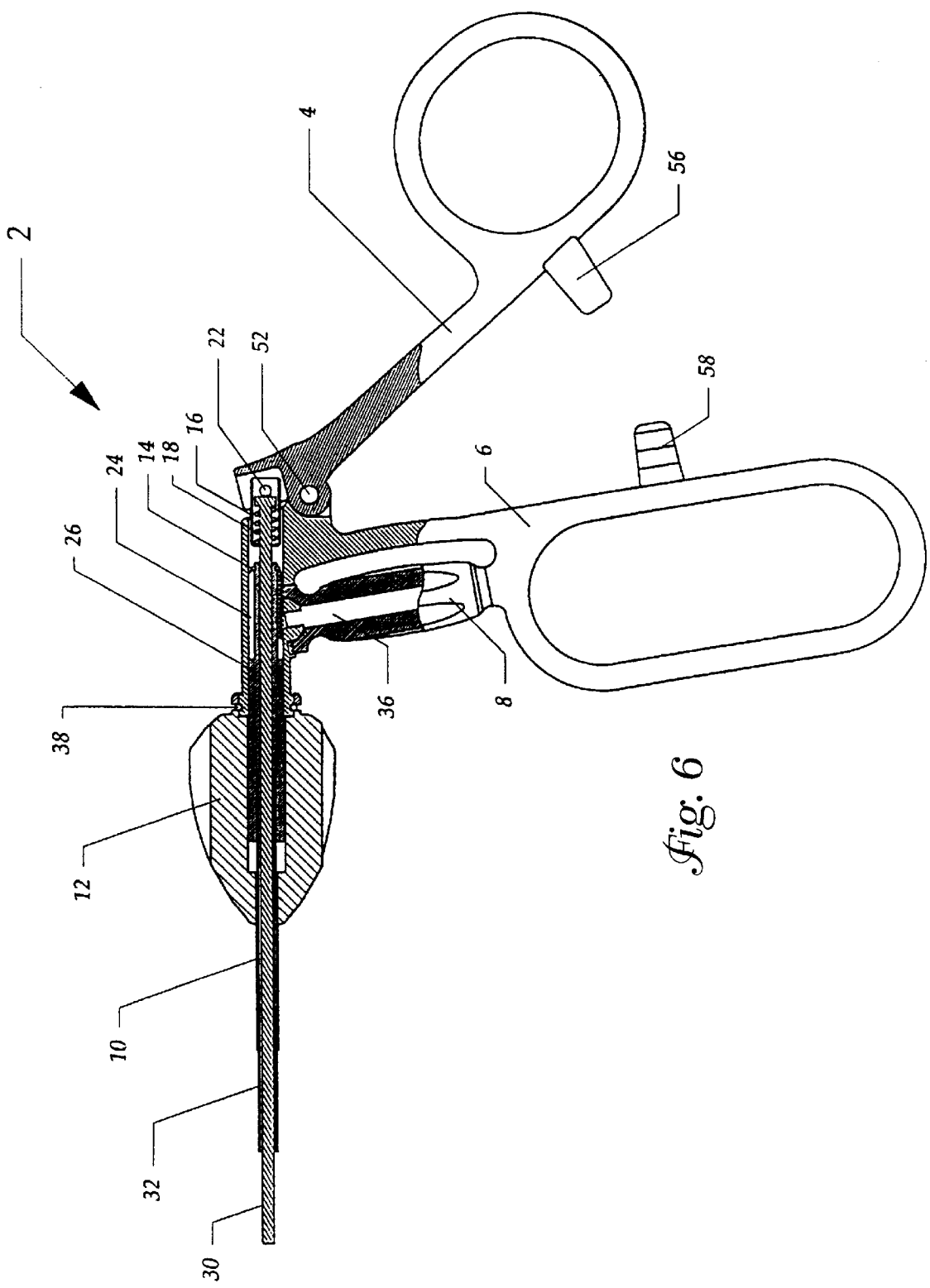
FIG. 6 is a left-side elevational view, partly in cross-section, of a handle assembly that may be used to operate the end effector.

FIG. 6 shows a handle assembly 2 that may be used with an end effector 1 in accordance with the present invention. Other controllers that are capable of imparting motion to end effector 1, eg., different handle designs or servo-motor mechanisms, could also be used. Generally, handle body 6 is held by either hand and with a thumb through trigger lever 4, leaving the index finger free to operate and rotate fingerwheel 8 and rotation knob 12. Trigger lever 4 may be moved toward handle body 6 to effect a grasping operation of end effector 1 by squeezing the thumb toward the other fingers. This squeezing motion causes trigger lever 4 to pivot about pin 52, so that the top of trigger lever 4 moves backward away from the rest of handle body 6.

Transverse pin 22 pivotably attaches cylinder 16 to thumb lever 4 so that cylinder 16 moves proximally when thumb lever 4 is squeezed. Control rod 30 has an enlarged head disposed inside cylinder 16 so that proximal motion of cylinder 16 is transferred to control rod 30. Motion of thumb lever 4 thereby results in motion of jaw 40 by way of transverse pin 22, cylinder 16, and control rod 30. Motion of thumb lever 4 toward handle 6 (i.e., squeezing motion) causes jaw 40 to clamp down against jaw 44 (see FIG. 2). Spring 18 is located inside cylinder 16 and rests between the enlarged head of control rod 30 and the end wall of cylinder 16. Spring 16 thereby serves as a force-limiting member that controls the maximum force that may be applied to control rod 30 so as to protect the jaws. Locking mechanisms, in the form of ratchet-type catches 56, 58, may be provided so that the surgeon may lock the jaws in a closed position.

A rotation actuator, in the form of rotation knob 12, may be provided to rotate the end effector mechanism. Rotation knob 12 is restrained from moving axially by spring clip or retaining ring 38 engaged in a cylindrical groove on handle housing 6. Although rotation knob 12 does not move axially with respect to handle body 6, it may rotate with respect to handle body 6. Rotation knob 12 is rigidly attached to tubular barrel 10 so that rotation of rotation knob 12 is transferred to tubular barrel 10.

Rotation may occur by application of force by the index finger to the outside of rotation knob 12. When rotation knob 12 rotates, the rotational force is transferred to tubular barrel 10. The rotational force is then passed to jaw 40 by pin 42 (see FIG. 2) and on to jaw 44, and control rod 30. Control rod 30 is free to rotate at its proximal end in cylinder 16.

Control tube 32 may be moved axially by barrel sleeve 26, which is a separate component from control tube 32 for manufacturing reasons, but is attached to control tube 32. Barrel sleeve 26 in turn extends through an interior channel of a control member, in the form of cylindrical hub rack 24. Barrel sleeve 26 is rotatably connected to hub rack 24 by retaining ring 14. Hub rack 24 and barrel sleeve 26 thus move axially together but are able to rotate independently. Therefore, when rotation knob 12 is rotated, hub rack 24 does not rotate even though barrel sleeve 26 may rotate. In addition, control rod 30 is free to slide axially inside barrel sleeve 26 and control tube 32.

To move jaw 44 axially and thereby roll a needle, hub rack 24 is moved axially, thereby moving barrel sleeve 26 and control tube 32 axially. Hub rack 24 is moved axially by rotating fingerwheel 8. Fingerwheel 8 is mounted on handle body 6 and has an axle 36. The axis of fingerwheel 8 may be tilted at an angle of approximately 80 degrees to the longitudinal axis of tubular barrel 10. Fingerwheel 8 has spiral gear teeth cut in its end face that mesh with gear teeth in the side of hub rack 24. Because the longitudinal axis of fingerwheel 8 is tilted, the gear teeth on fingerwheel 8 only mesh with the gear teeth on hub rack 24 on one side of fingerwheel 8 and do not interfere on the opposite side of fingerwheel 8.

In operation, rotation of fingerwheel 8 results in axial translation of hub rack 24, barrel sleeve 26, and control tube 32. Counter-clockwise rotation of fingerwheel 8 (as viewed from above) draws the elements proximally and thereby rolls the needle back toward the handle. Clockwise rotation of fingerwheel 8 pushes the elements distally and rolls the needle away from the handle (or clockwise when viewed from the left side).

Figure 7:
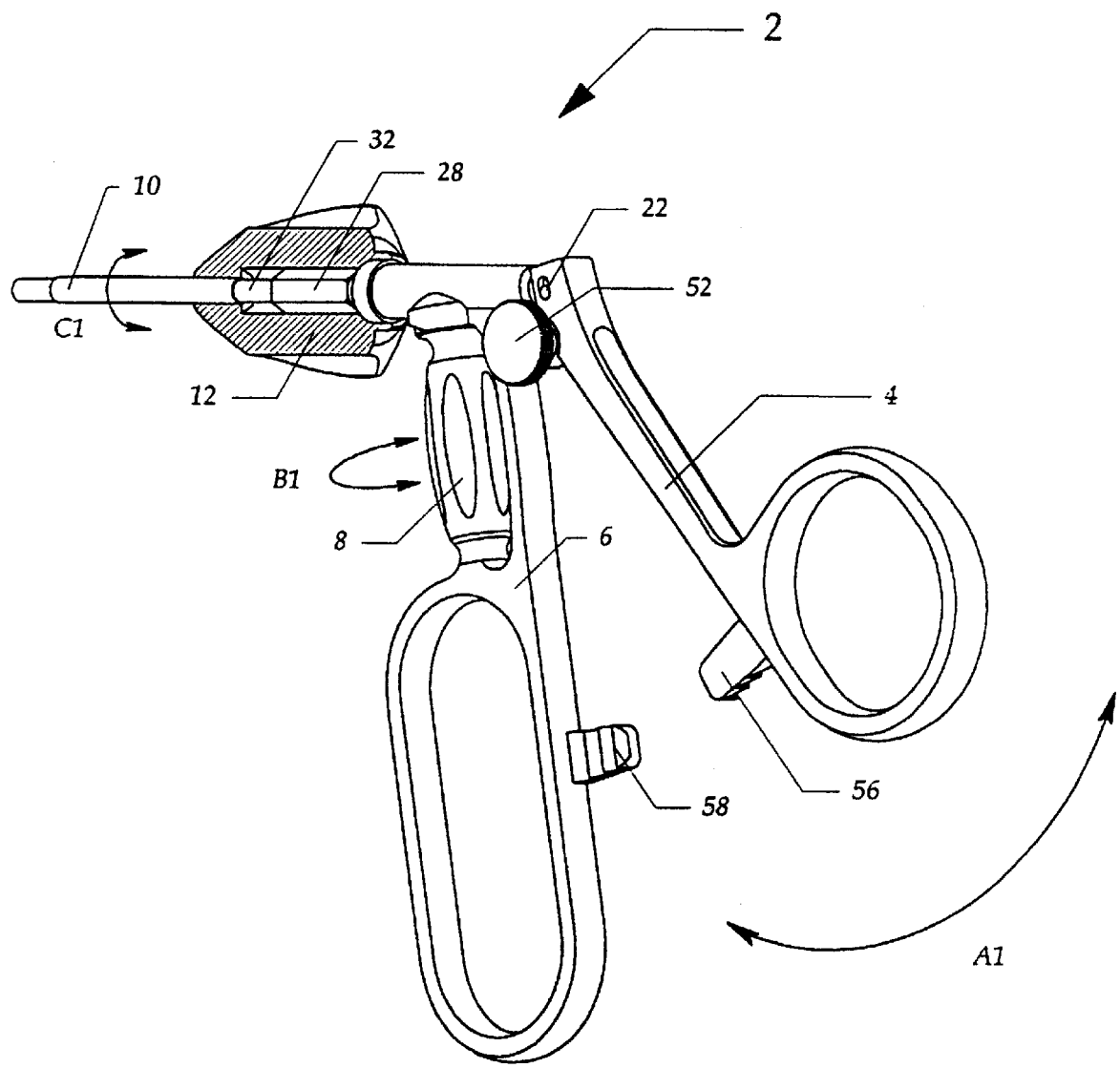
FIG. 7 is an isometric view of the handle assembly of FIG. 6.

FIG. 7 shows handle assembly 2 isometrically with rotation knob 12 partially cut away. The components of the barrel are shown connected together. Tubular barrel 10 is rigidly fixed to rotation knob 12, which is free to rotate relative to handle body 6 but is restrained from moving axially. Barrel sleeve 26 (see FIG. 6) is attached to the proximal end of control tube 32. The distal end of barrel sleeve 26 has a hexagonal section 28 which engages a hexagonal surface on the inside of rotation knob 12. Rotation of rotation knob 12 thereby rotates tubular barrel 10 and control tube 32. The rigid connections between these components helps prevent torsional windup.

Figure 8:
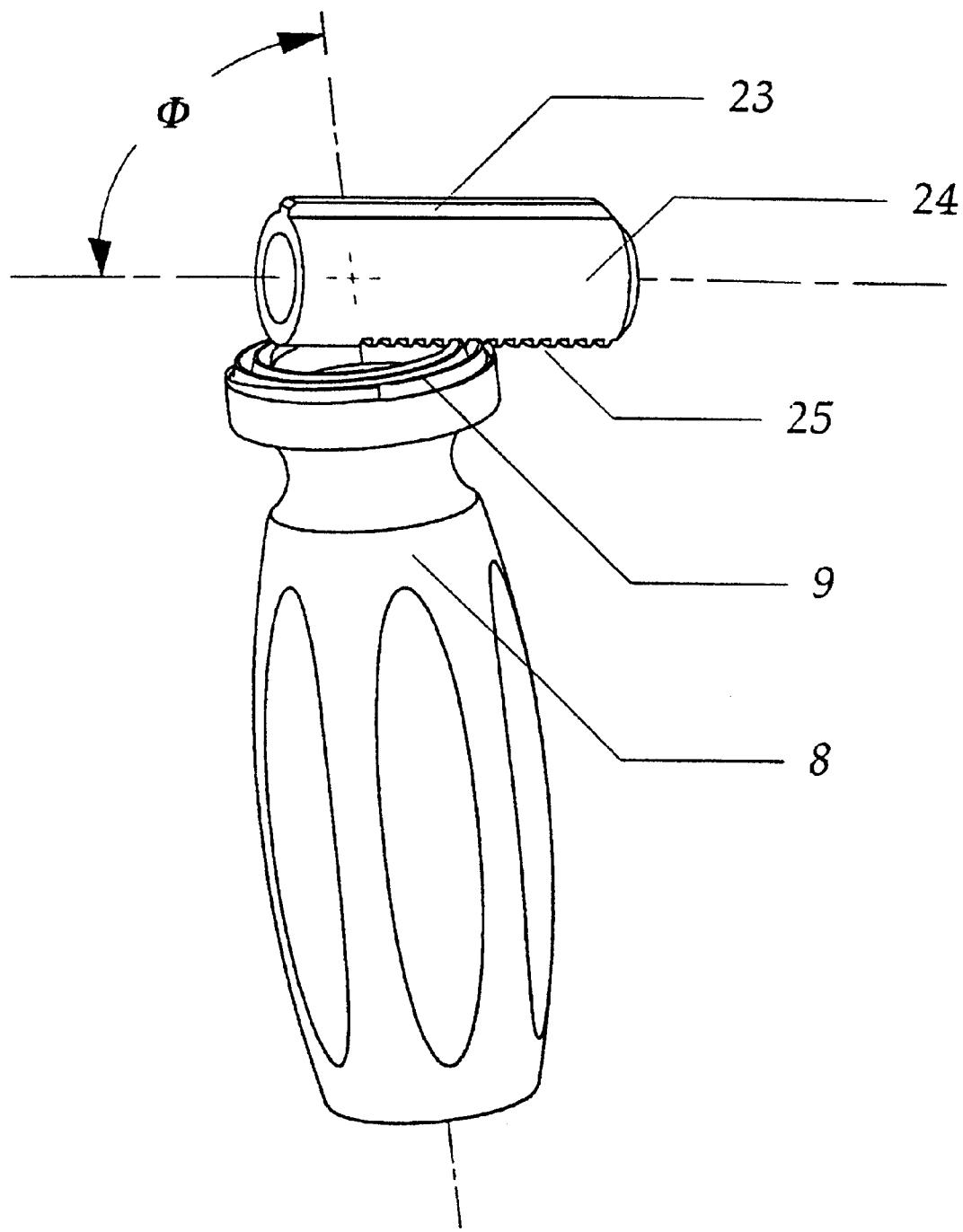
FIG. 8 is an isometric view of a fingerwheel and hub rack inside the handle shown in FIG. 6.

FIG. 8 is an isometric view of fingerwheel 8 and hub rack 24 showing the mating of the gear teeth 9, 25. Spiral-tooth gear 9 on the end of fingerwheel 8 engages curved-tooth rack 25 on hub rack 24 such that rotation of fingerwheel 8 causes axial translation of hub rack 24. A longitudinal key 23 may be provided for engagement with a reciprocal groove in the handle body (not shown) to prevent hub rack 24 from twisting or rotating during axial translation. Hub rack 24 may also beformed in an elengated geometric form, such as a hexagon, to resist rotation. The axis of fingerwheel 8 may be slightly inclined so that spiral-tooth gear 9 meshes with curve-tooth rack 25 on one side of fingerwheel 8 but does not interfere on the opposite side.

Figure 9A:
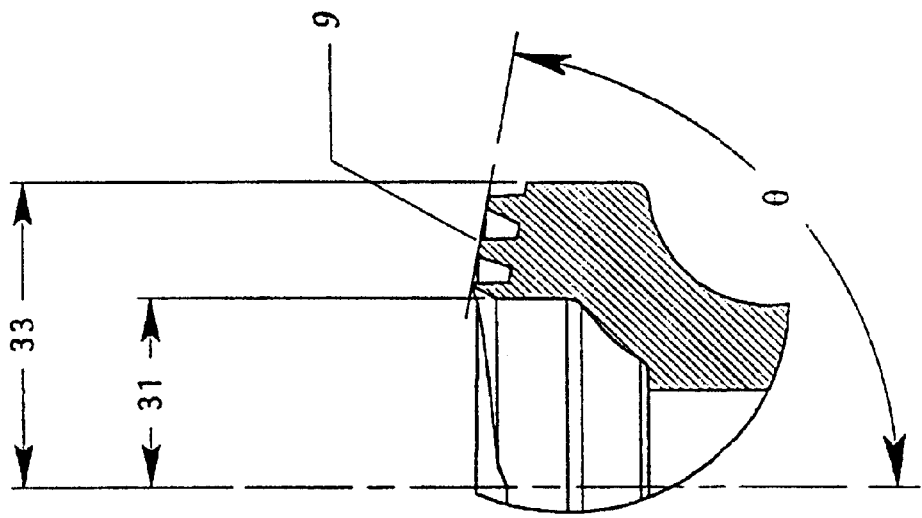
FIG. 9A is a section view showing the top portion of the fingerwheel of FIG. 8.
Figure 9B:
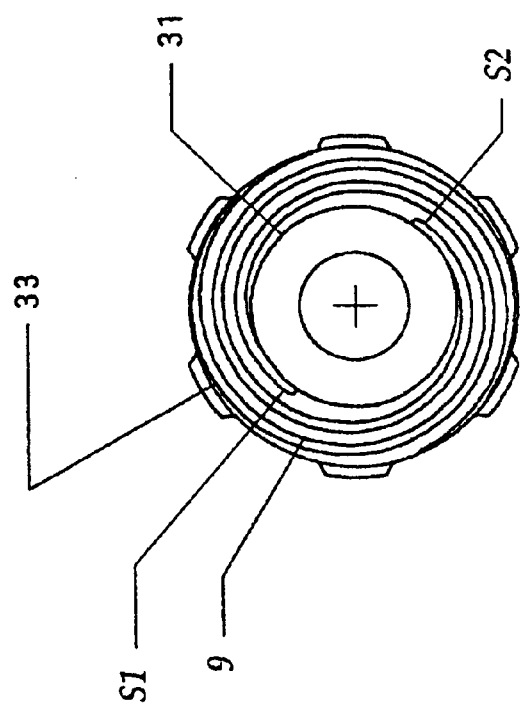
FIG. 9B is a top-end view of the fingerwheel of FIG. 8.

FIGS. 9A and 9B show spiral-tooth gear 9 in side cross section and end view, respectively. Spiral-tooth gear 9 is cut on a cone with an inclined angle, forming a three-dimensional spiral-helix. The cone may be at an 80 degree angle to the longitudinal axis of fingerwheel 8, as shown by the symbol theta. The angle could, however, range from 0 degrees to 90 degrees. The conical surface into which spiral-tooth gear 9 is cut is defined by an inside radius 31 of removed material and an outside radius 33. Spiral-tooth gear 9 may be cut as a "double start," meaning that there are two interleaved passes along the conical section, each 180 degrees out of phase with the other, as shown by S1 and S2 in the end view of fingerwheel 8 in FIG. 9B.

Figure 10B:
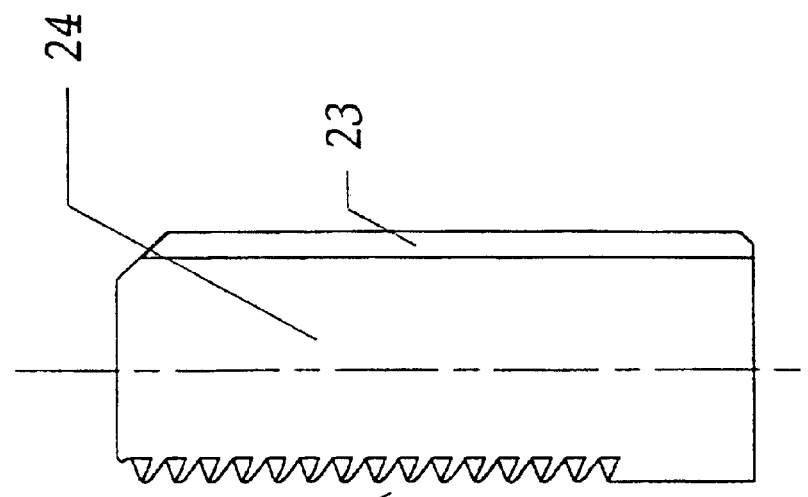
FIG. 10B is a side view of the hub rack of FIG. 8.
Figure 10A:
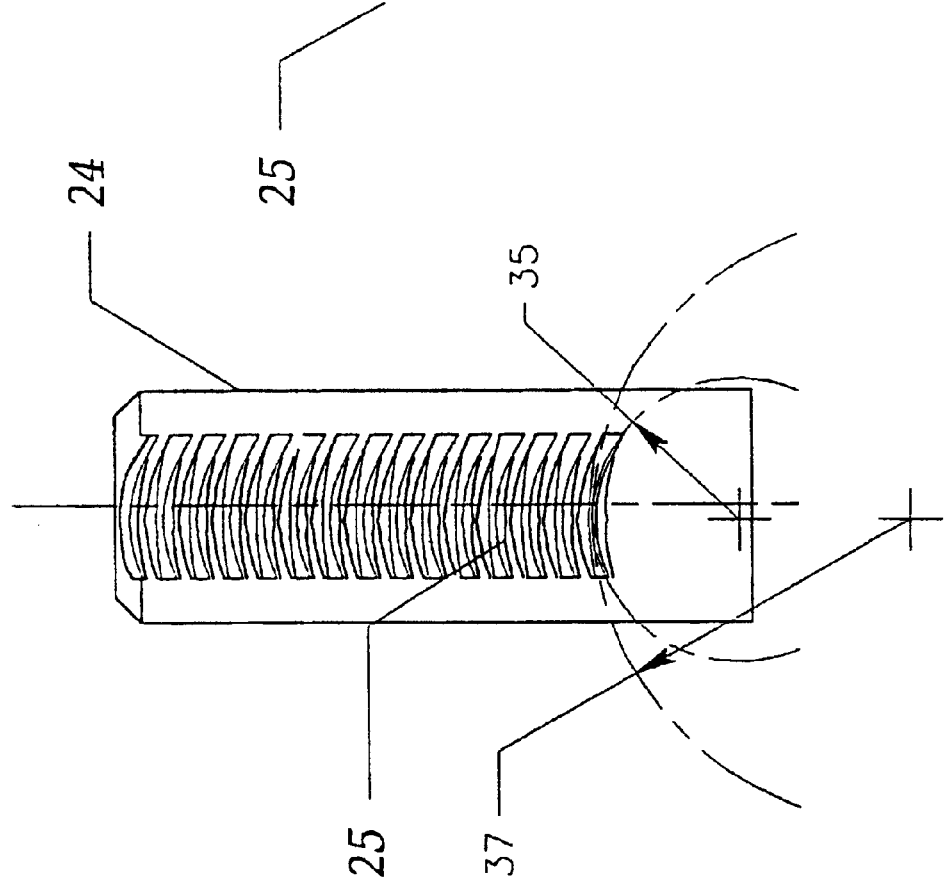
FIG. 10A is a view of the top side of the hub rack of FIG. 8.

FIGS. 10A and 10B show hub rack 24 in greater detail. To achieve more accurate engagement of the gear tooth surfaces, a curved-tooth profile 25 may be formed by standard tooth cut along two radii. The first radius 35 corresponds to the inside radius 31 of spiral-tooth gear 9, and the second radius 37 corresponds to the outside radius 33 of spiral-tooth gear 9. The paths of the two radial cuts making up the curved-tooth profile 25 may be tangent to one another and meet slightly offset from the projection of the center line upon the plane of the cut as shown in FIG. 10A. First radius 35 may be equal to inside radius 31, slightly greater than inside radius 31, or slightly less than inside radius 31. Second radius 37 is typically larger than outside radius 33.

Figure 11:
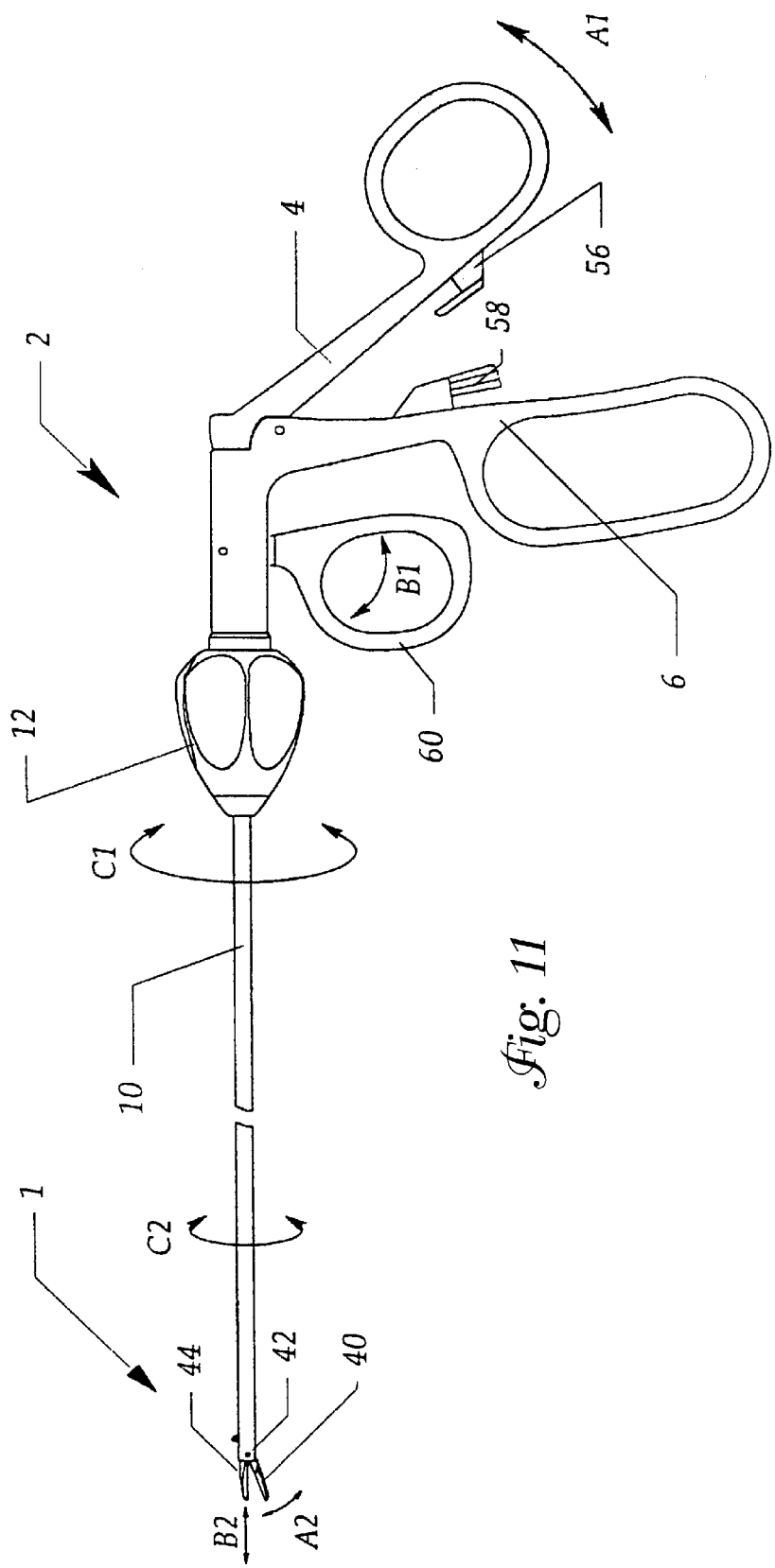
FIG. 11 is an elevational view showing an alternate handle assembly in accordance with the present invention.

FIG. 11 shows another handle assembly wherein a fingerloop 60 controls axial motion of jaw 44. As with the handle shown in FIG. 1, the surgical instrument has a handle assembly 2 on which is mounted a trigger lever 4. A rotation actuator, in the form of a rotation knob 12 may also be provided on handle assembly 2. Generally, handle body 6 may be held by a surgeon in either hand with a thumb through trigger lever 4, leaving the index finger to operate rotation knob 12 and fingerloop 60. A tubular barrel 10 may extend forward from handle assembly 2, with rotation knob 12 at its proximal end. Tubular barrel 10 also has at its distal end an end effector 1 which consists of a pair of end effector pieces, shown in the figures as jaws 40, 44. A pin 42 pivotably attaches jaw 40 to the distal end of tubular barrel 10.

Handle assembly 2 may be configured to produce three separate motions in end effector 1. First, rotation knob 12 may be turned to rotate tubular barrel 10 and thereby rotate end effector 1, as shown by rotation arcs C1 and C2. Second, trigger lever 4 may be squeezed toward handle assembly 2, as indicated by rotation arc A1, to cause jaw 40 to conduct a "grasping" motion relative to jaw 44, as indicated by rotation arc A2. Third, fingerloop 60 may be pulled in the proximal direction, as shown by arc B1, to make jaw 44 move proximally, as shown by arrow B2, and finger loop 60 may be pushed distally, as shown by arc B1, to make jaw 44 move distally, as shown by arrow B2. Axial sliding motion of jaw 44 may effect a rolling motion in a suture needle held between jaw 40 and jaw 44. Another form of a thumb lever lock is also shown by locking surfaces 56, 58.

Figure 12:
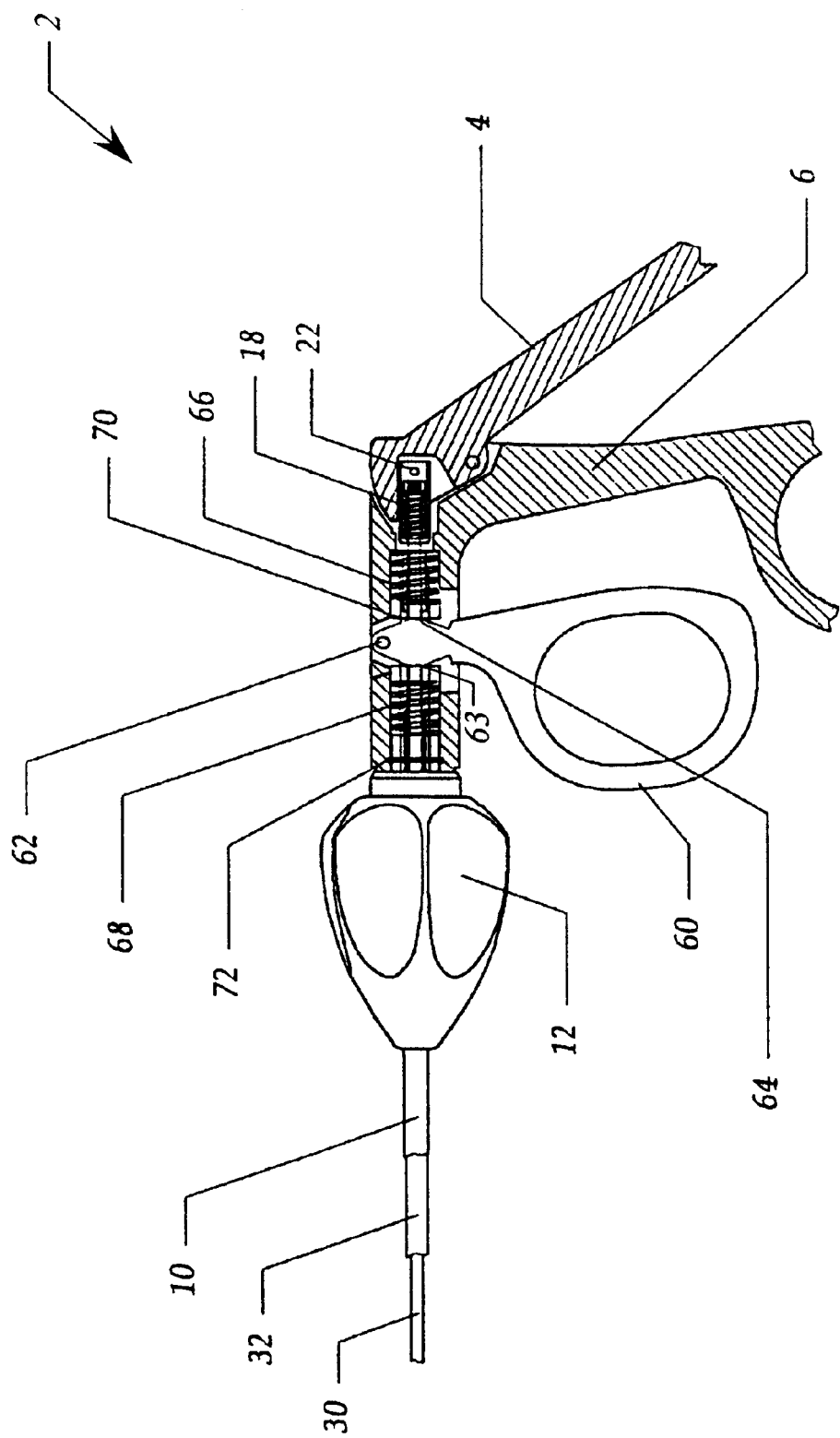
FIG. 12 is an elevational view, partially in section, showing the internal mechanisms of the handle assembly of FIG. 11.

FIG. 12 shows the internal mechanism of the handle assembly shown in FIG. 11. Fingerloop 60 is pivotably mounted on pin 62. Fingerloop 60 has a camming surface 64 on its proximal side internal to handle body 6. Camming surface 64 contacts a proximal portion of collar 70. Camming surface 63 on the side of fingerloop 60 opposite cam 64 contacts a distal portion of collar 70. Collar 70 may be attached to control tube 32 so that pivoting of fingerloop 60 counter-clockwise (i.e., pulling fingerloop 60 proximally) draws collar 70 proximally, thereby drawing control tube 32 and jaw 44 proximally. Likewise, pivoting of fingerloop 60 clockwise (i.e., pushing finger loop 60 distally) causes camming surface 63 to push against the distal portion of collar 70 and effect distal motion in collar 70, control tube 32, and jaw 44. Compression spring 66 bears against collar 70 on one end and against an interior surface of handle body 6 on its other end. Compression spring 68 bears against the end of rotation knob 12 on one end and against the distal portion of collar 70 on its other end. Together, compression springs 66, 68 provide counteracting biasing forces that cause fingerloop 60 to self-center when a surgeon releases pressure on fingerloop 60. FIG. 12 also shows rotation knob 12 rotatably attached to handle body 6 by a retaining ring 72 and fixedly attached to tubular barrel 10.

Figure 13:
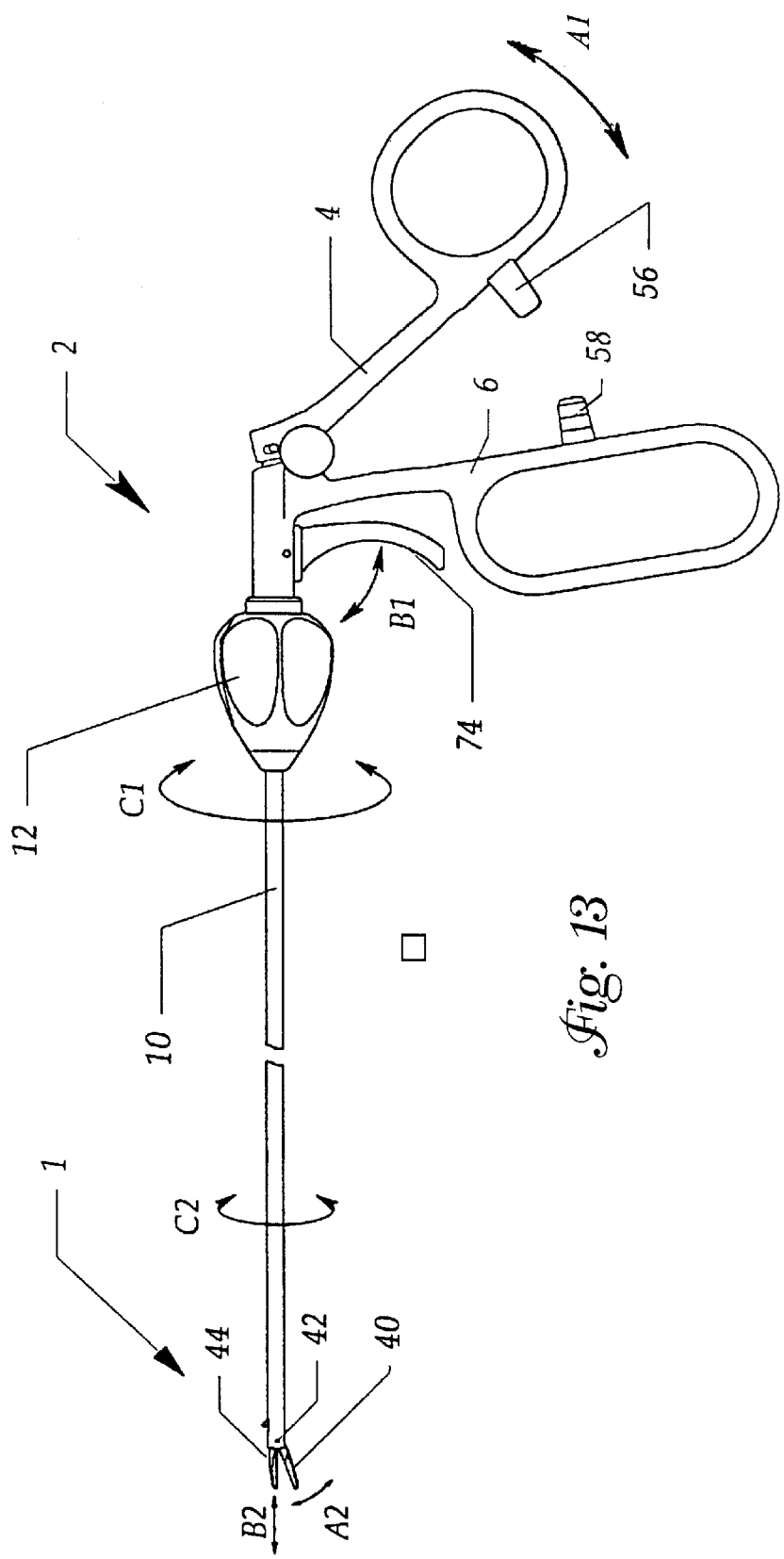
FIG. 13 is an elevational showing another handle assembly.

FIG. 13 shows another alternative handle assembly. Again, thumb trigger loop 4 is pivotably attached to handle body 6. Rotation knob 12 is rotatably attached to handle body 6 and is rigidly attached to tubular barrel 10. End effector 1, comprising pivoting jaw 40 and sliding jaw 44, is located at the distal end of tubular barrel 10. Sliding of jaw 44 is effected by finger trigger 74. Finger trigger 74 is operated by a pulling motion with an index finger, but is not normally moved by a pushing motion.

Figure 14:
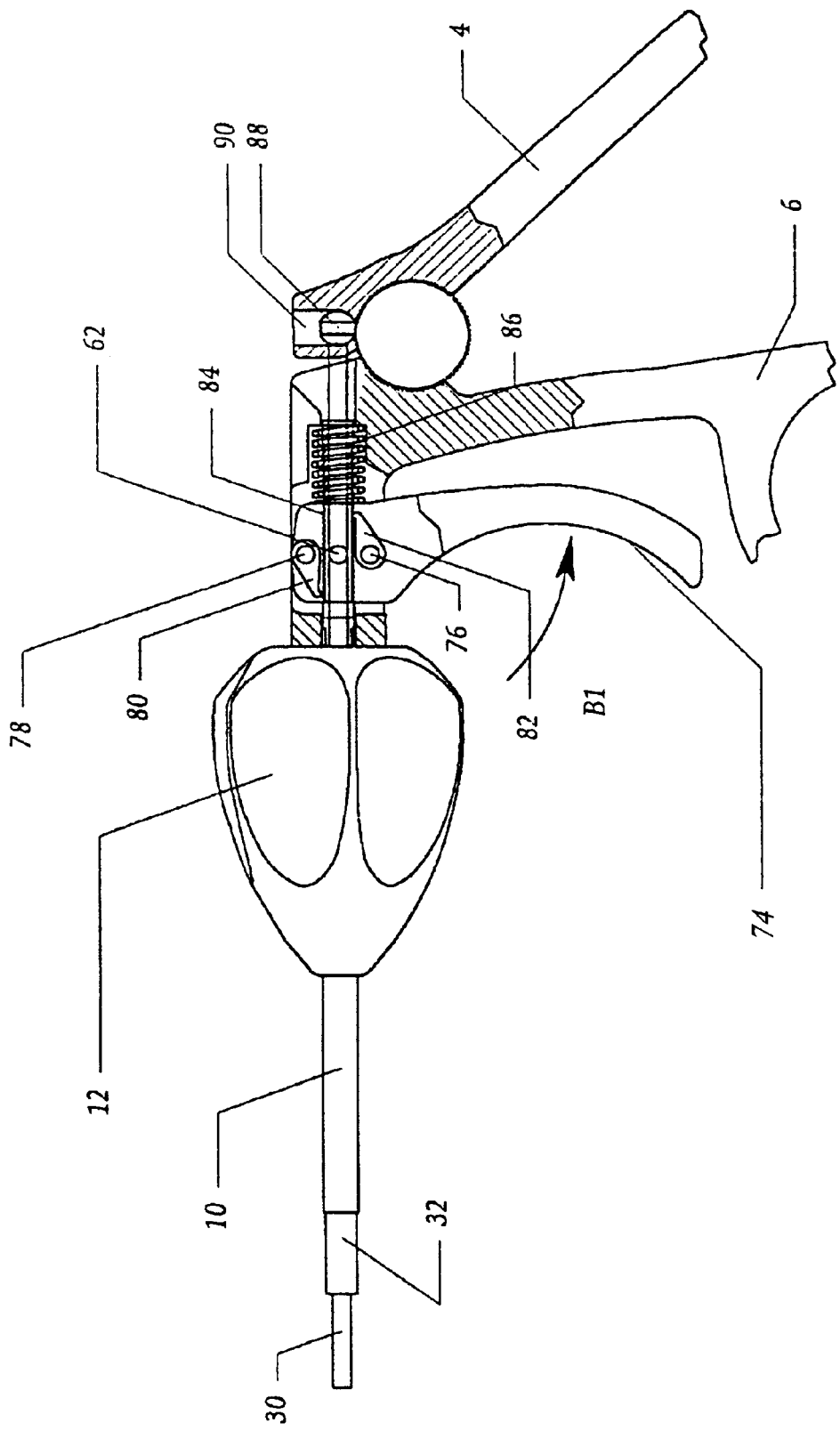
FIG. 14 is an elevational view, partially in section, showing the internal mechanisms of the handle assembly of FIG. 13.

FIG. 14 shows the mechanism of FIG. 13 in partial section and in more detail. Finger trigger 74 is pivotably mounted on pin 62, which is anchored in handle body 6 transverse to the longitudinal axis of tubular barrel 10. Upper pawl 80 and lower pawl 82 are pivotably mounted on pins 78, 76 which are attached to finger trigger 74 at distances roughly equidistant above and below the centerline of a rack 84 that is attached to control tube 32. Ratchet surfaces are cut into the perimeter of rack 84. The surfaces may be wholly around rack 84 or may be flat surfaces on two sides of rack 84. Pawls 80, 82 engage the ratchet surfaces of rack 84 under the biasing force of bias springs (not shown) which bias pawls 80, 82 into either engaged or disengaged position relative to rack 84. The action of pawls 80, 82 may be synchronized so that only one pawl is engaged at a time. The bias springs are disposed to toggle over center upon each movement of finger trigger 74. The springs thereby alternate which pawl is engaged, and also alter the direction of movement of rack 84. Rack 84 is rotatably attached to control tube 32 by a shoulder and retaining ring (not shown) so that control tube 32 is not fixed to rack 84, but instead may rotate with tubular barrel 10, and control rod 30, and rotation knob 12.

In operation, pulling finger trigger 74 in the proximal direction engages either upper pawl 80 or lower pawl 82, causing rack 84 to move either distally or proximally depending on which pawl is engaged. Finger trigger 74 may be return to its distal position under biasing force of spring 86, which bears against an inside wall of handle body 6 and against a proximal edge of finger trigger 74.

Successive pulls of finger trigger 74 cause alternating movement of sliding jaw 44. For example, a first proximal pull on finger trigger 74 moves sliding jaw 44 proximally, with movement of sliding jaw 44 proportional to movement of finger trigger 74. Releasing finger trigger 74 permits the bias springs on pawls 80, 82 to flip over center so that pawls 80, 82 are biased in the opposite direction. A second proximal pull on finger trigger 74 moves sliding jaw 44 distally a distance proportional to the amount of movement of finger trigger 74. Releasing finger trigger 74 again flips the bias springs so that pawls 80, 82 are back to their original positions. By pulling finger trigger 74 only to the point of pawl engagement, a surgeon can produce successive movements of jaw 44 in the same direction. In this manner, a surgeon could roll a suture needle a few degrees in one direction without either releasing or grabbing the needle, or rolling it in the wrong direction.

As an alternative design, pawls 80, 82 could be replaced with hardened metallic or non-metallic balls contained in specially-shaped cavities. The cavities could be shaped as narrowing raceways or pockets against which the balls would rest. Springs bearing directly on the balls could force the balls into engagement with ratchet 84. The balls could also be located in raceways or channels and contained in simple cages against which the bias springs could apply force.

FIG. 14 also shows a spherical ball 88 for transferring pivoting motion of thumb lever 4 into axial motion of control rod 30. Ball 88 is mounted at the proximal end of control rod 30 and engages a cylindrical pocket 90 on the top of thumb lever 4. Ball 88 permits control rod 30 to rotate with rotation knob 12 irrespective of the pivoted angle of thumb lever 4.

Figure 15:
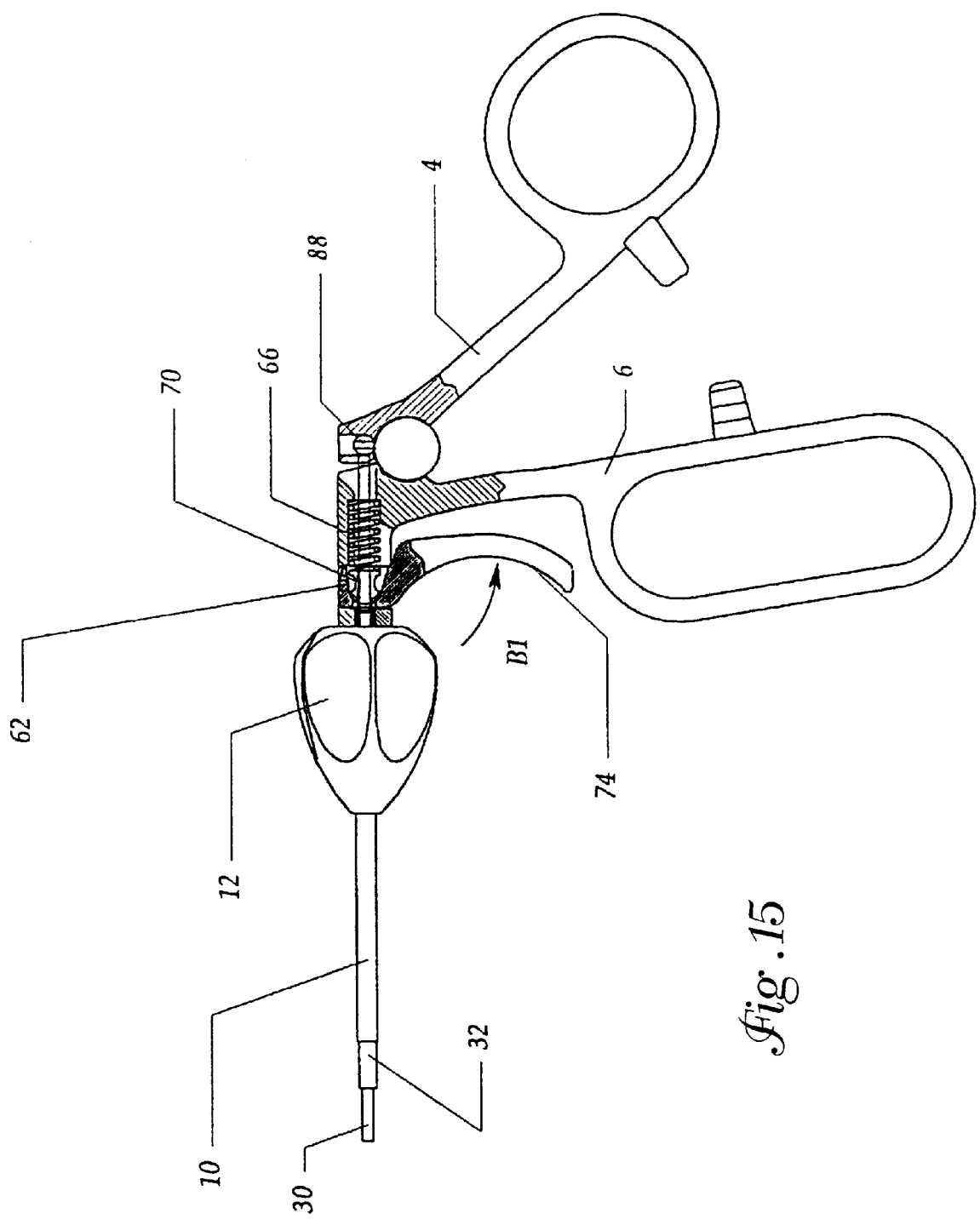
FIG. 15 is an elevational view, partially in section, showing an alternative embodiment of the internal mechanisms of the handle assembly of FIG. 13.

FIG. 15 shows another alternative handle assembly. The assembly includes a thumb lever 4 pivotably attached to a handle body 6, and a rotation knob 12 rotatably attached to handle body 6. Finger trigger 74 extends downward from handle body 6. Finger trigger 74 is pivotably mounted to handle body 6 by transverse pin 62. A collar 70 is biased against the distal side of finger trigger 74 below pin 62 by spring 66. Biasing force from spring 66 keeps finger trigger 74 biased in the distal direction and thereby keeps sliding jaw 44 (see FIG. 13), which is attached to finger trigger 74 by control tube 32, biased in the distal direction.

Finger trigger 74 may be pulled proximally by an index finger, as shown by arc B1, and may cause collar 70 to move proximally, drawing control tube 32 and sliding jaw 44 proximally. Position of finger trigger 74 and jaw 44 may directly correlate with each other. Fully pulling finger trigger 74 in the proximal direction causes jaw 44 to move to its fully proximal position.

In operation, a needle may be rolled between jaws 40, 44 by first grasping the needle (by squeezing thumb lever 4) and then pulling on finger trigger 74 to cause jaw 44 to move proximally. Rolling a needle in the opposite direction may be accomplished by first pulling on finger trigger 74, and then grasping the needle (by squeezing thumb lever 4) and releasing finger trigger 74 to cause jaw 44 to move distally. Increased pressure on thumb lever 4 results in a firmer grasp by jaw 40 on the needle. Increased force by jaw 40 increases the frictional force on the needle, locking sliding jaw 44 into position and decreasing the tendancy of the needle to roll.

Figure 16:
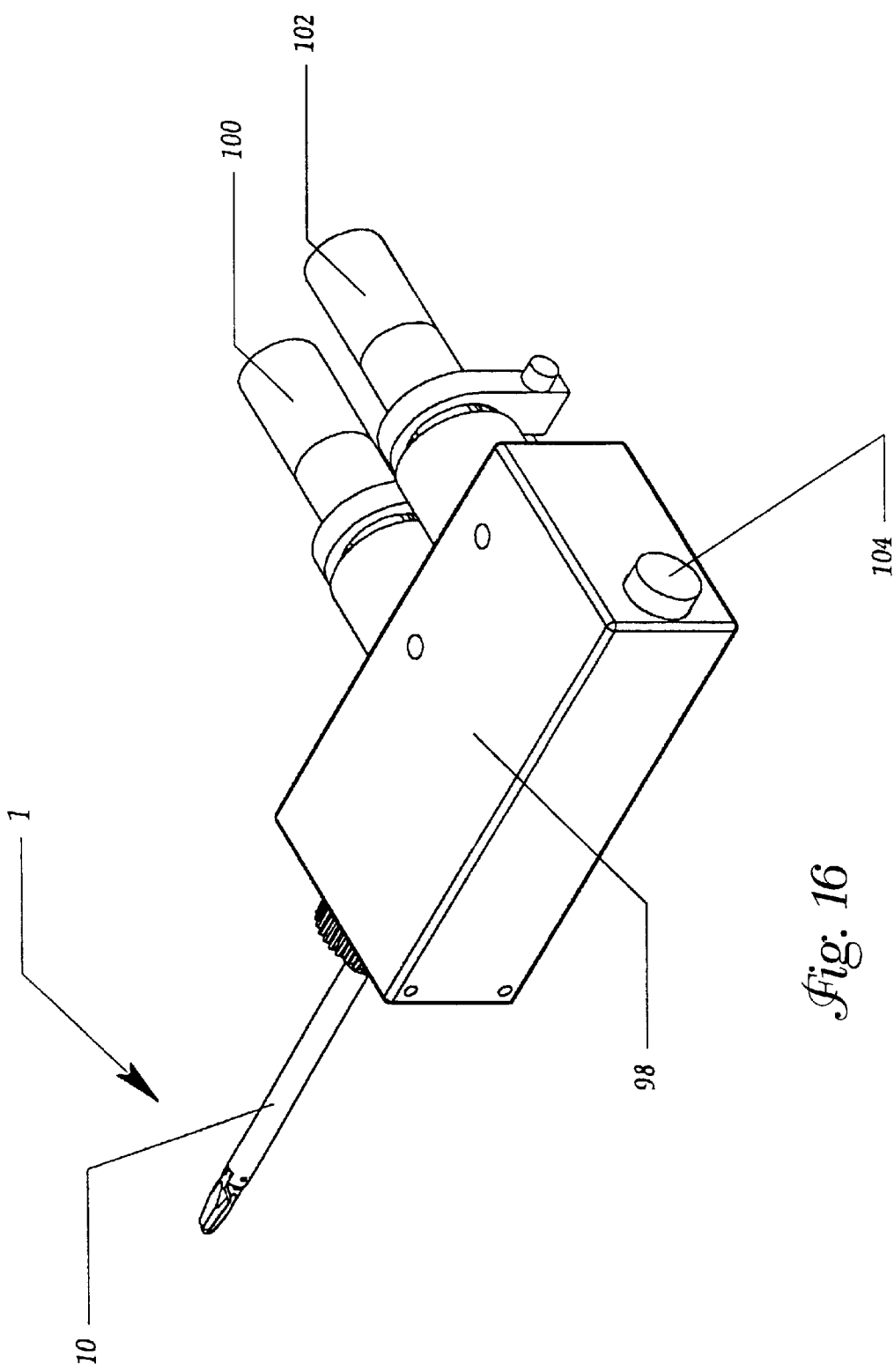
FIG. 16 is an isometric view of a motor-powered handle assembly.
Figure 18:
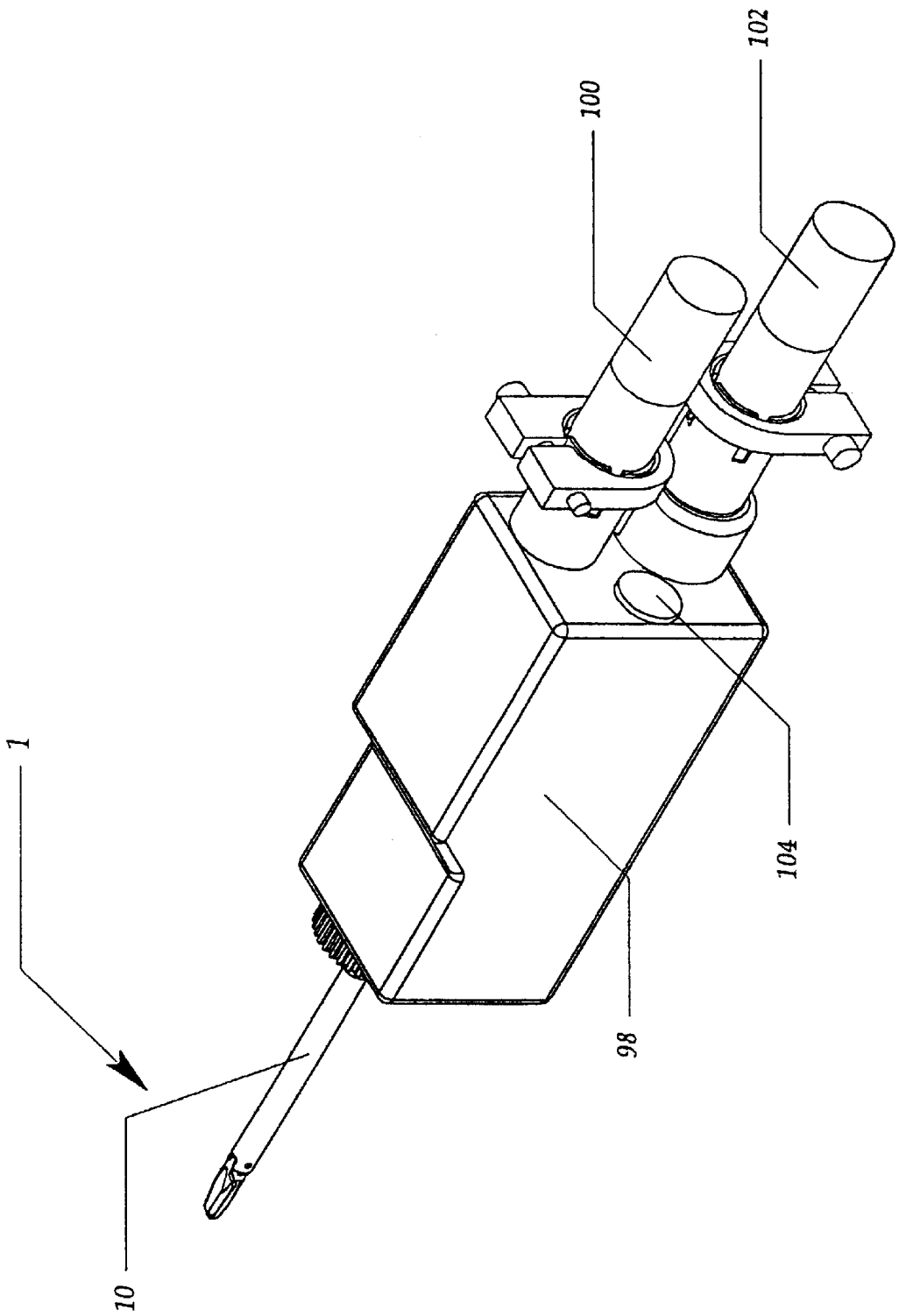
FIG. 18 is an isometric view of another motor-powered handle assembly.

FIGS. 16 and 18 show perspective views of two embodiments in which tubular barrel 10 and end effector assembly 1 may be coupled to a series of servomotors to enable surgery by a surgical robot. The device may be mounted on the end of a robot arm, which is not shown. The servomotors may be connected to the end effector assembly by force transducers and position encoders under microprocessor control. In FIGS. 16 and 18, tubular barrel 10 and the control members have been shortened to show the entire device.

Figure 17:
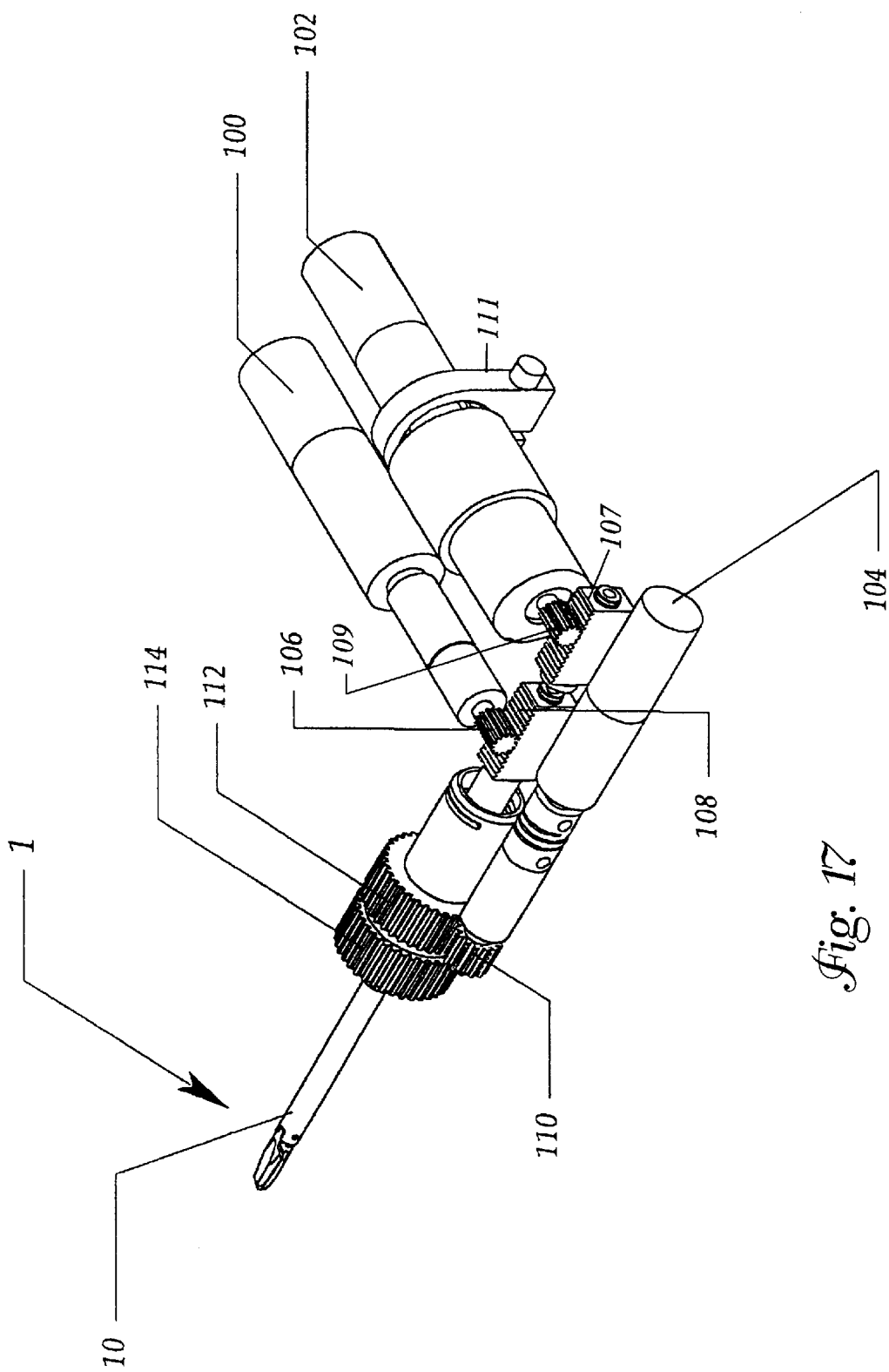
FIG. 17 is a perspective view of the handle assembly shown in FIG. 16 with the external housing removed for clarity.

FIG. 16 shows the housing 98 with servomotors 100, 102 having longitudinal axes which are transverse to the longitudinal axis of tubular barrel 10. In FIG. 17, end effector assembly 1 is captured by a disconnecting mechanism in hub 114 which is attached to spur gear 112. Spur gear 112 meshes with pinion 110, which is driven by rotation servomotor 104. Thus, operation of rotation servomotor 104 causes rotation of tubular barrel 10 and end effector assembly 1.

Sliding jaw 44 (see FIG. 1) may be moved by control tube 32 (shown in FIGS. 2–4) which may be rotatably attached to rack member 108. Control tube 32 thus moves axially with rack member 108 but may rotate with respect to rack member 108. Rack member 108 may alternatively be cylindrical and may be rigidly attached to control tube 32, so that rack member 108 rotates with tubular barrel 10 and disconnect hub 114. Rack member 108 may translate in the axial direction under force from pinion 106 attached to gearmotor 100. Thus, rotational force from gearmotor 100 may be translated through rack member 108 and control tube 32 to cause axial translation of slidable jaw 44.

Pivoting jaw 40 (see FIG. 1) may be moved by control rod 30 (shown in FIGS. 2–4) which may be rotatably attached to rack member 107. Control rod 30 thus moves axially with rack member 107 but may rotate with respect to rack member 107. Rack member 107 may alternatively be cylindrical and may be rigidly attached to control rod 30, so that rack member 107 rotates with tubular barrel 10 and disconnect hub 114. Rack member 107 may translate in the axial direction under force from pinion 109 attached to gearmotor 102. Thus, rotational force from gearmotor 102 may be translated through rack member 107 and control rod 30 to cause pivoting of pivoting jaw 40. Servomotors 100, 102, 104 may be anchored by mounts attached to the housing (not shown), such as mount 111.

Figure 19:
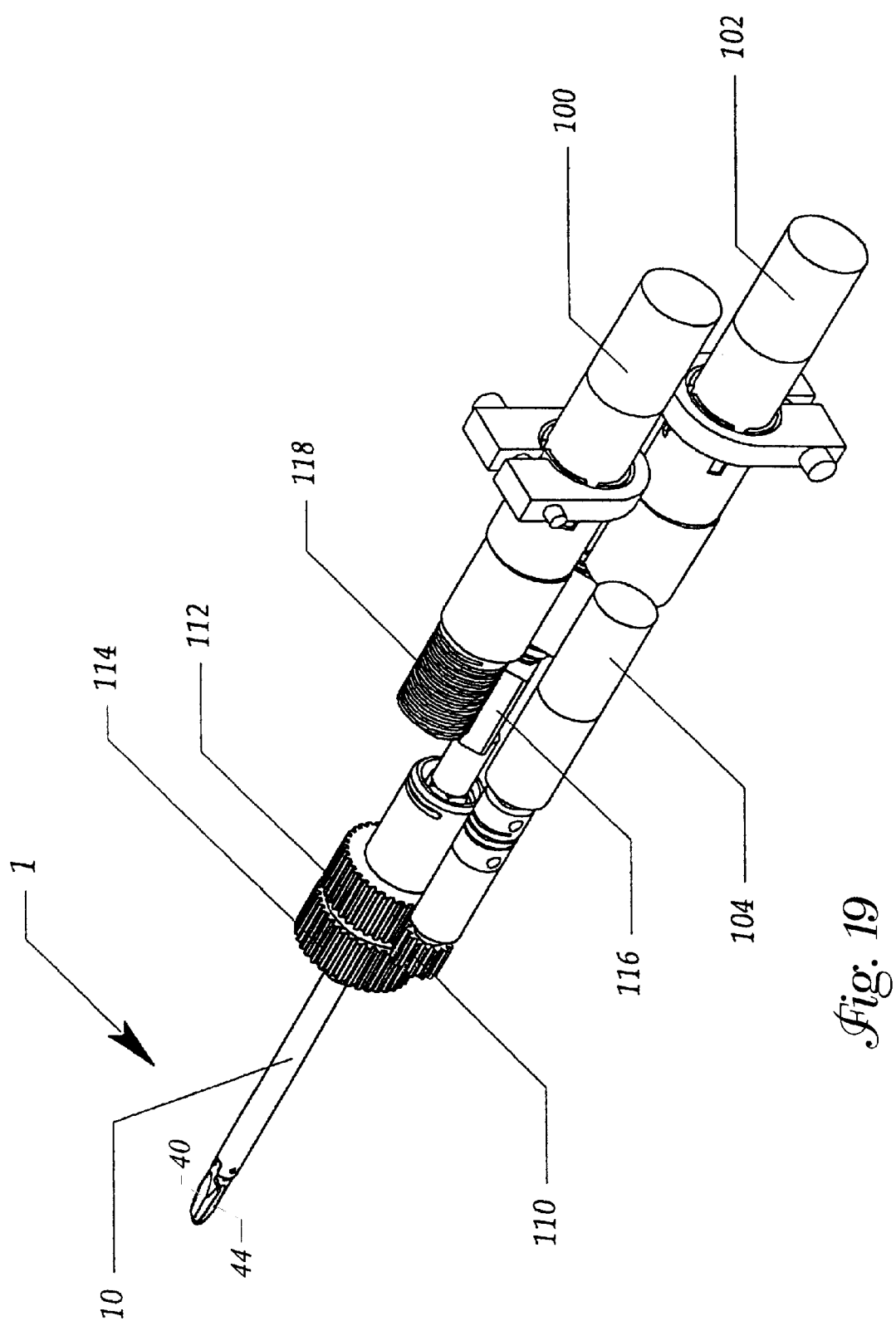
FIG. 19 is a perspective view of the handle assembly shown in FIG. 18 with the external housing removed for clarity.

FIG. 18 shows a handle assembly in which the longitudinal axes of the servomotors 100, 102 lie parallel to the longitudinal axis of tubular barrel 10. In FIG. 19, end effector 1 is captured by a disconnecting mechanism in hub 114 which is attached to spur gear 112. Spur gear 112 meshes with pinion 110, which is driven by rotation servomotor 104. Thus, operation of rotation servomotor 104 causes rotation of tubular barrel 10 and end effector assembly 1.

Sliding jaw 44 may be moved by control tube 32 (shown in FIGS. 2–4), which may have a helical screw 116 cut about its proximal end. The helical screw on control tube 32 may mate with helical screw 118 on a shaft or gear mesh extending from servomotor 100. The longitudinal axis of servomotor 100 is parallel to the longitudinal axis of control tube 32 so that the helical screws 116, 118 mate cleanly. Rotational force from servomotor 100 is transferred into axial motion by the helical screws 116, 118 and causes control tube 32 and sliding jaw 44 to move axially.

Likewise, pivoting jaw 40 may be moved by control rod 30 (shown in FIGS. 2–4) which may have a helical screw (not shown) cut about its proximal end. The helical screw on control rod 30 may mate with a helical screw (not shown) on a shaft or gear mesh extending from servomotor 102. The longitudinal axis of servomotor 102 is parallel to the longitudinal axis of control rod 30 so that the helical screws mate cleanly. Rotational force from servomotor 102 is thus transferred into axial motion by the helical screws and causes control rod 30 to move axially and jaw 40 to pivot. On either servomotor 100 or servomotor 102, the screws may take the form of male screws (as shown) mating with female screws on control tube 32 and control 30. Alternatively, the forms could be female screws mating with male screws.

Figure 20:
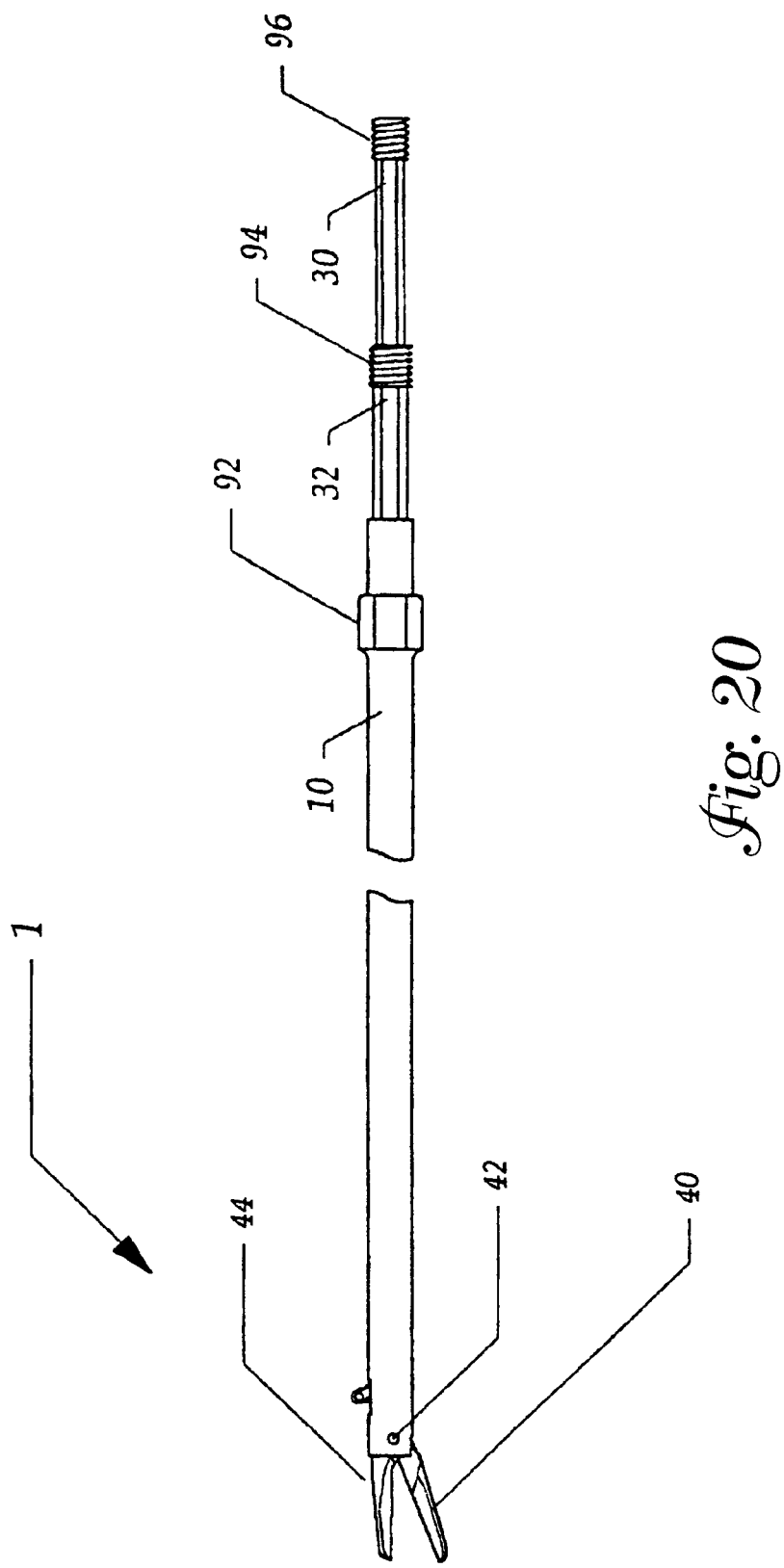
FIG. 20 shows a detachable end effector in accordance with the present invention.

FIG. 20 shows a detachable end effector unit that may be used with a motorized handle. End effector assembly 1 consists of jaw 40 pivotably attached to tubular barrel 10, and jaw 44 slidably disposed at the distal end of tubular barrel 10. Disconnect coupling 92 is located at the proximal end of tubular barrel 10. Disconnect coupling 92 may snap into hub 114, as shown in FIGS. 17 and 19. Control tube 32 has a coupling 94 at its proximal end. Control rod 30 has a coupling 96 at its proximal end. Coupling 94 may be rigidly attached to control tube 32 so that both axial and rotational motion may be imparted to control tube 32 by coupling 94. Likewise, coupling 96 may be rigidly attached to control rod 30 so that both axial and rotational motion may be imparted to control rod 30 by coupling 96. Couplings 94, 96 may be comprised of, or may be attached to, hub racks, cylinders or collars, or any other structure that may impart appropriate motion to jaws 40, 44. Couplings 94, 96 are shown in FIG. 20 having rack-tooth profiles, but they could also have helical screw threads, bayonet-style fittings, ball-and-detent snap fittings, or other conventional or quick-connect attachment mechanisms.

Figure 21A:
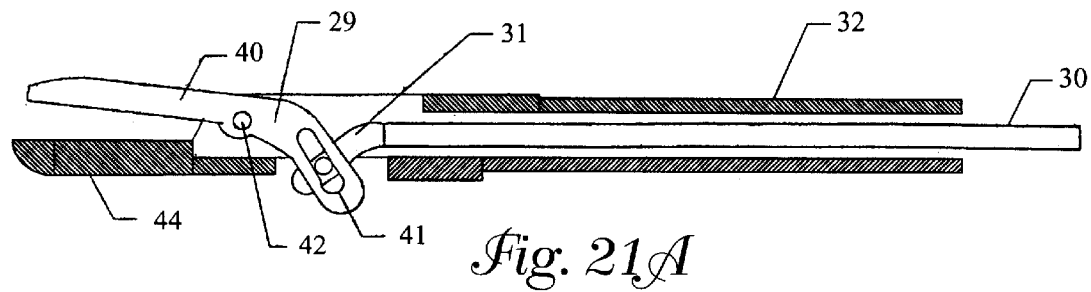
FIG. 21A is a left-side section view of another embodiment of the end effector mechanism showing the pivoting of the jaw.
Figure 21B:
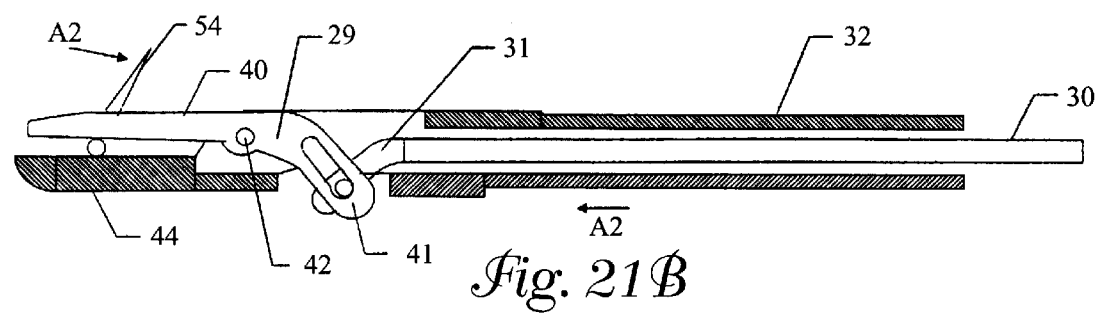
FIG. 21B is a left-side section view of the end effector shown in FIG. 21A, showing the rolling of a needle.

FIGS. 21A and 21B show another embodiment of the end effector mechanism, showing the pivoting of the jaw. Control rod 30 extends through the interior of control tube 32 and has link 31 connected to its distal end. Link 31 has a pin 39 connected transversely to the longitudinal axis of control rod 30. Pin 39 is inserted into slot 41. Slot 41 is cut in jaw 40, which pivots on pin 42. Pin 42 is attached to tubular barrel (not shown). Slot 41 is located proximally to pin 42, while the clamping portion of jaw 40 is located distally to pin 42. When control rod 30 is pushed distally with respect to the tubular barrel (not shown) in which pin 42 is mounted, pin 39 rides up slot 40, which is cut at an angle relative to the motion of pin 39. As pin 39 moves distally in slot 41, it causes jaw 40 to open away from jaw 44. When control rod 30 is pulled proximally with respect to the tubular barrel, pin 39 moves proximally is slot 41 and causes jaw 40 to close toward jaw 44, as shown in FIG. 21B. In this manner, jaw 40 can be closed to hold a needle 54 against jaw 44.

Rolling of needle 54 is also shown in FIG. 21B. With jaw 40 closed against jaw 44 so as to hold needle 54 tightly, control tube 32 may be moved in the distal direction, as shown by arrow A1. Axial motion of control tube 32 is translated into axial motion of jaw 44. When jaw 44 moves, a shearing force is applied to needle 54 by jaw 40 and jaw 44. The needle therefore rotates in the clockwise direction, as shown by rotation arc A2. Axial motion of control tube 32 in the proximal direction may likewise produce rolling of needle 54 in the counter-clockwise direction.

Figure 22A:
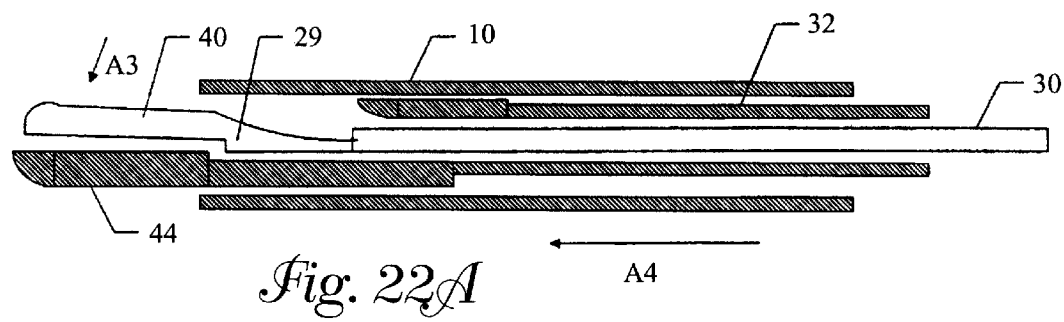
FIGS. 22A and 22B are left-side section views of another embodiment of the nd effector mechanism showing pivoting of the jaw.
Figure 22B:
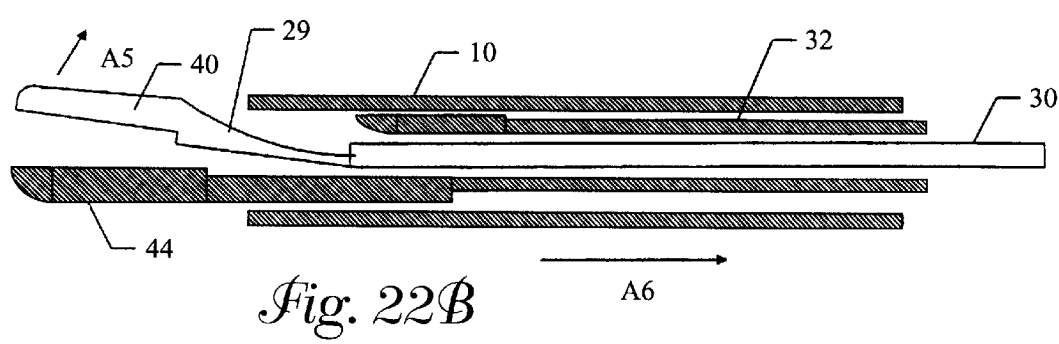

FIGS. 22A and 22B show another embodiment of the end effector. Control rod 30 and control tube 32 are disposed within tubular barrel 10. Jaw 44 is attached to the distal end of control tube 32. Jaw 40 is attached to the distal end of cantilever spring 29 which is in turn attached to the distal end of control rod 30. Cantilever spring 29 is normally biased outward so that jaw 40 moves away from jaw 44. The distal edge of tubular barrel 10 contacts the upper edge of cantilever spring 29 and limits the opening motion of cantilever spring 29. Cantilever spring 29 increases in thickness from its proximal end to its distal end. Therefore, as cantilever spring 29 is drawn into tubular barrel 10 by distal motion of tubular barrel 10, as shown by arrow A6, cantilever spring 29 pivots counter-clockwise and jaw 40 is forced downward toward jaw 44, as shown by rotation arc A3. When tubular barrel 10 is drawn proximally with respect to control rod 30, as shown by arrow A6, cantilever spring 29 forces jaw 40 away from jaw 44 under the natural outward bias of cantilever spring 29.

A number of embodiments of the present invention have been described. Nevertheless, it will be understood that various modifications may be made without departing from the spirit and scope of the invention. As one example, the end effector could be attached to any device that is capable of transmitting motion to the end effector pieces. Accordingly, other embodiments are within the scope of the following claims.

What is claimed is:

1. A surgical instrument comprising:
   a first linkage member having a proximal end and a distal end;
   a first jaw operably connected to the distal end of the first linkage member;
   a second linkage member having a proximal end and a distal end; and
   a second jaw operably connected to the second linkage member and adjacent the first jaw, wherein the second jaw is slidable relative to the first jaw.

2. The surgical instrument of claim 1, wherein the first jaw is pivotable about a fixed axis.

3. The surgical instrument of claim 1, further comprising a pivot pin that is fixedly attached to the instrument, wherein the first jaw pivots about the pivot pin.

4. The surgical instrument of claim 1, wherein the first jaw is pivotable through an arc.

5. The surgical instrument of claim 1, wherein the second jaw is pivotable about a fixed axis.

6. The surgical instrument of claim 1, wherein the first jaw defines an internal recess.

7. The surgical instrument of claim 1, wherein the first jaw defines outer edges, and the first jaw is recessed along the outer edges.

8. The surgical instrument of claim 1, wherein the first jaw includes a first gripping surface and the second jaw includes a second gripping surface, the second gripping surface being textured.

9. The surgical instrument of claim 8, wherein the first gripping surface is textured.

10. The surgical instrument of claim 8, wherein the second gripping surface comprises a high-friction material.

11. The surgical instrument of claim 8, wherein the second gripping surface comprises a high-hardness material.

12. The surgical instrument of claim 11, wherein the second gripping surface comprises a tungsten carbide insert.

13. The surgical instrument of claim 8, wherein the first gripping surface defines an internal recess.

14. The surgical instrument of claim 8, wherein the first gripping surface defines outer edges, and the first gripping surface is recessed along the outer edges.

15. The surgical instrument of claim 1, further comprising a camming surface on the first linkage member and a camming surface on the first jaw, the camming surfaces being connected by contact with each other.

16. The surgical instrument of claim 1, wherein the first linkage member is pivotably connected to the first jaw.

17. The surgical instrument of claim 16, wherein the first linkage member and the first jaw are connected such that movement of the first linkage member in a direction toward its distal end causes the first jaw to pivot in a first direction, and movement of the first linkage member toward its proximal end causes the first jaw to pivot in an opposite direction.

18. The surgical instrument of claim 16, wherein the first linkage member and the first jaw are connected such that movement of the first linkage member toward its distal end causes the first jaw to pivot away from the second jaw, and movement of the first linkage member toward its proximal end causes the first jaw to pivot toward the second jaw.

19. The surgical instrument of claim 1, wherein the second linkage member is rigidly connected to the second jaw.

20. The surgical instrument of claim 19, wherein the second linkage member and the second jaw are connected such that movement of the second linkage member toward its distal end causes the second jaw to translate axially away from the distal end of the instrument, and movement of the second linkage member toward its proximal end causes the second jaw to translate toward the proximal end of the instrument.

21. The surgical instrument of claim 19, wherein the first linkage member is movable independent of the second linkage member.

22. The surgical instrument of claim 1, further comprising a control actuator operably connected to the first linkage member, wherein movement of the control actuator in a first direction causes the first linkage member to move the first jaw in a first direction, and movement of the control actuator in another direction causes the first linkage member to move the first jaw in a second direction.

23. The surgical instrument of claim 1, further comprising a rolling actuator operably connected to the second linkage member, wherein movement of the rolling actuator in a first direction causes the second linkage member to move the second jaw in a first direction, and movement of the rolling actuator in another direction causes the second linkage member to move the second jaw in a second direction.

24. The surgical instrument of claim 1, further comprising a tubular member having a proximal end and a distal end, wherein the first linkage member and the second linkage member are slidably disposed substantially inside the tubular member.

25. The surgical instrument of claim 24, further comprising a rotation actuator coupled to the tubular member, whereby operation of the rotation actuator transmits rotational force to the tubular member, the first jaw, and the second jaw.

26. The surgical instrument of claim 25, wherein the rotation actuator comprises a servomotor.

27. The surgical instrument of claim 23, further comprising a housing connected to the proximal end of the tubular member.

28. The surgical instrument of claim 27, wherein the tubular member is detachably connected to the housing.

29. The surgical instrument of claim 28, further comprising a first threaded portion on the tubular member and a second threaded portion on the housing, whereby the first threaded portion may be operably connected to the second threaded portion.

30. The surgical instrument of claim 27, further comprising a control actuator attached to the housing and operably connected to the first linkage member, whereby operation of the control actuator produces axial translation of the first linkage member.

31. The surgical instrument of claim 30, wherein the control actuator comprises a servomotor.

32. The surgical instrument of claim 30, wherein movement of the control actuator in a first direction causes the first linkage member to translate in a direction toward the distal end of the tubular member, and movement of the control actuator in another direction causes the first linkage member to translate in a direction toward the proximal end of the tubular member.

33. The surgical instrument of claim 32, wherein the control actuator comprises a thumb trigger lever.

34. The surgical instrument of claim 33, further comprising a trigger lock in operable connection with the thumb trigger lever.

35. The surgical instrument of claim 27, further comprising a rolling actuator attached to the housing and operably connected to the second linkage member, whereby operation of the rolling actuator produces axial translation of the second linkage member.

36. The surgical instrument of claim 35, wherein operation of the rolling actuator causes an object held between the first jaw and the second jaw to rotate about its own axis.

37. The surgical instrument of claim 35, wherein rotation of the rolling actuator in a first direction causes the second linkage member to move the second jaw toward the distal end of the instrument, and rotation of the rolling actuator in a second direction causes the second linkage member to move the second jaw toward the proximal end of the instrument.

38. The surgical instrument of claim 37, wherein the rolling actuator comprises a fingerwheel.

39. The surgical instrument of claim 38, wherein the fingerwheel is operable by a user's index finger.

40. The surgical instrument of claim 38, further comprising a first mating surface attached to the fingerwheel and a second mating surface attached to the second linkage member, whereby the first mating surface contacts the second mating surface and rotation of the fingerwheel results in axial translation of the second linkage member.

41. The surgical instrument of claim 40, wherein the first mating surface is located on the top surface of the fingerwheel.

42. The surgical instrument of claim 41, wherein the first mating surface comprises a helical gear.

43. The surgical instrument of claim 41, wherein the first mating surface comprises a spiral gear and the second mating surface comprises a rack having a gear pattern that mates with the spiral gear.

44. The surgical instrument of claim 35, wherein the rolling actuator comprises a finger loop, whereby motion of the finger loop in a first direction causes the second linkage member to move the second jaw toward the distal end of the instrument, and motion of the finger loop in a second direction causes the second linkage member to move the second jaw toward the proximal end of the instrument.

45. The surgical instrument of claim 44, further comprising a first ratchet surface attached to the fingerloop and a second ratchet surface attached to the second linkage member, wherein motion of the fingerloop causes the first ratchet surface to move relative to the second ratchet surface.

46. The surgical instrument of claim 35, wherein the rolling actuator comprises a servomotor.

47. A surgical instrument comprising:
a first linkage member and a second linkage member;
a first jaw operably connected to the first linkage member;
a second jaw operably connected to the second linkage member; and
a gripping surface coupled to the second jaw, wherein the gripping surface is slidable relative to the first jaw, and the jaws may be moved toward each other and away from each other.

48. A surgical instrument comprising:
a tubular member having a proximal end and a distal end;
a first linkage member slidably disposed inside the tubular member;
a first jaw comprising a rigid portion and a flexible portion, the jaw being attached to a distal end of the first linkage member and extending from the distal end of the tubular member;
a second linkage member slidably disposed within the tubular member;
a second jaw operably connected to the distal end of the second linkage member;
wherein linear translation of the first linkage member in a proximal direction causes the first jaw to close relative to the second jaw.

49. A surgical instrument comprising:
a tubular member having a proximal end and a distal end;
a first end effector piece having a first gripping surface and mounted near the distal end of the tubular member;
a second end effector piece having a second gripping surface and disposed near the distal end of the tubular member and adjacent the first end effector piece, wherein the second end effector piece is slidable relative to the first end effector piece, and wherein the first end effector piece may close relative to the second end effector piece to hold a surgical item placed between the first end effector piece and the second end effector piece.

50. A surgical instrument comprising:
an elongated member having a proximal end and a distal end; and
a needle roller mounted at the distal end of the elongated member, wherein a needle having a longitudinal axis held in the needle roller may be rolled about an axis that is substantially parallel to the longitudinal axis.

51. A surgical instrument comprising:
an elongated member having a distal end and a proximal end;
first and second end effectors disposed at the distal end of the tubular member, wherein the end effectors define a needle retention area; and
a control member coupled to move one of the end effectors relative to the other of the end effectors to roll a needle having a longitudinal axis within the needle retention area, about an axes that is substantially parallel to the longitudinal axis of the needle.

52. A method for manipulating a surgical needle, the method comprising:

providing a surgical instrument having a proximal end and a distal end, the surgical instrument comprising a first jaw pivotably mounted near the distal end of the surgical instrument, and a second jaw disposed adjacent the first jaw, wherein the second jaw is slidable relative to the first jaw;

placing a needle between the first jaw and the second jaw.

53. A needle roller comprising:

a first jaw;

a second jaw adjacent to the first jaw and slidable relative to the first jaw, wherein a needle placed between the first jaw and the second jaw may be rolled when the first jaw is slid relative to the second jaw.

\* \* \* \* \*